US007211420B1

(12) United States Patent
Wong et al.

(10) Patent No.: US 7,211,420 B1
(45) Date of Patent: May 1, 2007

(54) PROCESS FOR OXIDIZING TERPENES

(75) Inventors: Luet Lok Wong, Oxford (GB); Stephen Graham Bell, Oxford (GB); Angus Bishop Carmichael, Oxford (GB)

(73) Assignee: ISIS Innovation Limited (GB)

( * ) Notice: Subject to any disclaimer, the term of this patent is extended or adjusted under 35 U.S.C. 154(b) by 0 days.

(21) Appl. No.: 09/856,339

(22) PCT Filed: Nov. 19, 1999

(86) PCT No.: PCT/GB99/03873

§ 371 (c)(1),
(2), (4) Date: Aug. 15, 2001

(87) PCT Pub. No.: WO00/31273

PCT Pub. Date: Jun. 2, 2000

(30) Foreign Application Priority Data

Nov. 19, 1998 (GB) .................................. 98254212

(51) Int. Cl.
- C12N 9/02 (2006.01)
- C12N 15/00 (2006.01)
- C12Q 1/00 (2006.01)
- C12Q 1/68 (2006.01)
- C07H 21/04 (2006.01)
- A01N 25/00 (2006.01)

(52) U.S. Cl. ............................... 435/189; 435/4; 435/6; 435/25; 435/440; 536/23.2; 536/23.7; 514/789

(58) Field of Classification Search ................ 435/189, 435/172.3, 68.1, 69.1, 132, 4, 440, 6, 25; 536/23.2, 23.7; 514/789
See application file for complete search history.

(56) References Cited

U.S. PATENT DOCUMENTS

| 5,763,237 | A | | 6/1998 | Savithiry et al. |
| 6,100,074 | A | * | 8/2000 | Flitsch et al. ................ 435/189 |
| 6,117,661 | A | * | 9/2000 | Wong et al. ................. 435/189 |

FOREIGN PATENT DOCUMENTS

| GB | 0334841 | | 9/1993 |
| GB | 2294692 | | 5/1996 |
| GB | 2 306 485 | A * | 5/1997 |

(Continued)

OTHER PUBLICATIONS

W. M. Atkins et al., Molecular Recognition in Cytochrome P-450: Alteration of Regioselective Alkane Hydroxylation via Protein Engineering, Amer. Chem. Soc., 2715-2716 (1989).

(Continued)

*Primary Examiner*—P. Achutamurthy
*Assistant Examiner*—Yong D. Pak
(74) *Attorney, Agent, or Firm*—Fulbright & Jaworski LLP

(57) ABSTRACT

A process for oxidizing a substrate which is an acyclic or cyclic terpene, or a cycloalkene; or a substituted derivative thereof, which process comprises oxidizing said compound with a mutant haem-containing enzyme, the mutant comprising the substitution of an amino acid in the active site by an amino acid with a less polar side-chain. The enzyme is typically $P450_{cam}$ or $P450_{BM-3}$. Cells and libraries of cells in which the process can be carried out or which can be used to select advantageous mutant enzymes are also provided.

6 Claims, 4 Drawing Sheets

FOREIGN PATENT DOCUMENTS

| GB | 2 306 485 A1 | 7/1997 |
|---|---|---|
| WO | 88/01641 A1 | 3/1988 |
| WO | 94/01564 A1 | 1/1994 |
| WO | 96/14419 A1 | 5/1996 |
| WO | 97/16553 A1 | 5/1997 |

OTHER PUBLICATIONS

O. Sibbesen et al., Putidaredoxin Reductase-Putidaresoxin-Cytochrome P450cam Triple Fusion Protein, J. Bio. Chem., 22462-22469 (1996).

C. Oliver et al., A Single Mutation in Cytochrome P450 BM3 Changaes Substrate Orienation in a Catalytic Intermediate and the Regiospecificity of Hydroxylation, 1567-1572 (1997).

P. England et al., The oxidation of naphthalene and pyrene by cytochrome P450cam,FEBS Letters 424, 271-174 (1998).

W. Atkins et al., The Roles of Active Site Hydrogen Bonding in Cytochrome P-450 cam as Revealed by Site-directed Mutagenesis, J. Bio Chem., 18842-18849 (1988).

International Search Report, PCT/GB99/03873, May 23, 2000.

Nickerson, Darren P., et al.; The catalytic activity of cytochrome $P450_{cam}$ towards styrene oxidation is increased by site-specific mutagenesis; FEBS Letters 405 (1997), pp. 153-156.

Jones, Nia E., et al.; Engineering the selectivity of aliphatic C-H bond exidation catalysed by cytochrome P450cam; Chem. Commun., vol. 21, pp. 2413-2414, 1996.

Tuck, Stephen F., et al.; Active Sites of the Cytochrome $p450_{cam}$ (CYP101) F87W and F87A Mutants; The Journal of Biological Chemistry, vol. 268 (1), pp. 269-275, Jan. 5, 1993.

Filipovic, D., et al.; Ethylbenzene Hydroxylation by Cytochrome :$450_{cam}$; Biochemical and Biophysical Research Communications, vol. 189 (1), pp. 488-495, Nov. 30, 1992.

Dong, Jinsheng, et al.; Coexpression of Mammalian Cytochrome P450 and Reductase in *Escherichia coli*; Archives of Biochemistry and Biophysics, vol. 327 (2), pp. 254-259, 1996.

Atkins, William M., et al.; Molecular Recognition in Cytochrome P-450: Alteration of Regioselective Alkane Hydroxylation via Protein Engineering; J. Am. Chem. Soc., vol. 111, pp. 2715-2717, 1989.

White, Ronald E., et al.; Regioselectivity in the Cytochromes P-450: Control by Protein Constraints and by Chemical Reactivities; Archives of Biochemistry and Biophysics, vol. 228 (2), pp. 493-502, Feb. 1, 1984.

Loida, Paul J., et al.; Molecular Recognition in Cytochrome P-450: Mechanism for the Control of Uncoupling Reactions; Biochemistry, vol. 32, pp. 11530-11538, 1993.

De Primo, Carmelo, et al.; Mutagenesis of a Single Hydrogen Bond in Cytochrome P-450 Alters Cation Binding and Heme Solvation; The Journal of Bioogical Chemistry, vol. 265 (10), pp. 5361-5633, 1990.

Shimoji, Miyuki, et al.; Design of a Novel P450: A Functional Bacterial—Human Cytochrome P450 Chimera; Biochemistry, vol. 37, pp. 8848-8852, 1998.

Gooch, Jay W., et al.; Effects of *ortho*- and Non-*ortho*-Substituted Polychlorinated Biphenyl Congeners on the Hepatic Monooxygenase System in Scup (*Stenotomus chrysops*); Toxicology and Applied Pharmacology 98, 422-433 (1989).

Hegg, Eric L., et al.; Herbicide-Degrading α-Keto Acid-Dependent Enzyme TfdA: Metal Coordination Environment and Mechanistic Insights; Biochemistry 1999; 38 16714-16726.

Gotoh, Osamu; *Substrate Recognition Sites in Cytochrome P450 Family 2 (CYP2) Proteins Inferred from Comparative Analyses of Amino Acid and Coding Nucleotide Sequences*; J. Biol. Chem.; Jan. 5, 1992; pp. 83-90, vol. 267; The American Society for Biochemistry and Molecular Biology, Inc.; U.S.A.

Bogaards, Jan J.P.; *Human Cytochrome P450 Enzyme Selectivities in the Oxidation of Chlorinated Benzens*; Toxicology and Applied Pharmacology; 1995; pp. 44-52, vol. 132; Academic Press, Inc.; U.S.A.

Mueller, Ernest J., Loida, Paul J.; Sligar, Stephen G.; *Twenty-five Years of P450cam Research—Mechanistic Insights into Oxygenase Catalysis*; Cytochrome P45: structure, Mechanism and Biochemistry: $2^{nd}$ ed. Paul R. Ortiz de Montellano Ed, Plenum Press, New York 1995, pp. 83-124.

\* cited by examiner

PROCESS FOR OXIDIZING TERPENES

The invention relates to a process for enzymatically oxidising terpenes and cycloalkenes.

Terpenoid compounds are widespread in biological systems and constitute one of the largest class of natural products. They are major constituents of essential oils, some of which are of considerable value in the flavour and perfume industries. Many terpenoids are also biologically active. Some are anti-bacterial and anti-fungal agents and thus are of great interest to the pharmaceutical industry. Indeed, terpenoids are some of the highest added value chemicals.

The terpenoids of commercial interest are not normally the terpenes themselves, but rather derivatives which commonly require stereoselective functionalisation at allylic as well as non-activated carbon-hydrogen bonds of the parent terpene. This type of chemical transformation is one of the most difficult reaction to carry out by conventional methods of chemical synthesis—the highly reactive chemical oxidising agents required are non-selective and typically they will preferentially attack more activated carbon-hydrogen bonds and reactive functional groups such as olefinic double bonds commonly present in terpenes.

The present invention concerns the enzymatic oxidation of terpenes and cycloalkenes. This technique enables the synthesis of hydroxylated terpenes (and cycloalkenes), often in a single step, and provided that the match between substrate and enzyme is correct, the oxidation reaction can be highly chemoselective (attack at a particular functional group such as a non-activated C—H bond rather than some other reactive functional group) and stereoselective. The fine tuning and alterations of substrate specificity and selectivity of substrate oxidation are very difficult to achieve for conventional reagents.

The present invention provides a process for oxidising a substrate which is an acyclic or cyclic terpene or a cycloalkene, or a substituted derivative thereof, which process comprises oxidising said compound with a mutant haem-containing enzyme, the mutant comprising the substitution of an amino acid in the active site by an amino acid with a less polar side-chain.

Although the terpenes used in the present invention will generally have the formula $(C_5H_8)_n$ where n is 2 or more, especially 2, 3 or 4, it is to be understood that the term "terpene" extends to compounds which are strictly referred to as "terpenoid", involving the loss or shift of a fragment, generally a methyl group. Thus, for example, sesquiterpenes (where n is 3) which can be used in the present invention may contain only, say, 14, rather than 15, carbon atoms. Generally the terpene is one which can be built up from isoprene units. The terpene may be cyclic or acyclic.

The monoterpenes (where n is 2) will generally have 10 carbon atoms, typically with 1 to 3 double bonds, especially 1 or 2 ring double bonds, and typically with 0 to 2 rings. It is possible for one of the rings to be formed as a bridge containing, typically 0 or 1 carbon atoms. In other words, it can be formed by a direct link between 2 carbon atoms of an existing ring or with an intermediate methylene group. If the terpene is acyclic it will generally contain at least 2 double bonds and generally 3.

The sesquiterpenes will normally contain 14 or 15 carbon atoms, typically with 0 to 2 double bonds and typically 1 to 3 rings, with the possibility of fused rings and/or bridged rings.

The rings which may be present in the terpenes will typically have from 3 to 9 carbon atoms, more especially 5 or 6 carbon atoms. Thus, in particular, the terpenes will contain a cyclohexane, or cyclohexadiene ring.

The terpenes will generally contain a total of 3 or 4 exocyclic methyl or methylene groups, for example 2 methyl groups and 1 methylene group or 3 methyl groups for a monoterpene, and 3 methyl groups and 1 methylene group or 4 methyl groups for a sesquiterpene.

The monoterpene is typically a limonene, pinene, terpinene, sabinene, thujene, mercene, ocimeme, nerol or geraniol, for example as shown in Table 1.

The sesquiterpene is generally formed by a head-to-tail arrangement of three isoprene units. The sesquiterpene is typically an aromadendrene, caryophyllene, longifolene, valencene, isobazzanene, silphinene, ishwarane, isopatchoul-3-ene, or isosesquicarene, for example as shown in Table 2.

The diterpene (where n is 4) is typically casbene, retinal, abietic acid or a gibberellin.

The cycloalkene generally comprises up to 9 ring members, e.g. it is a 5, 6, 7, 8, 9 or more membered ring. The cycloalkene is typically a cyclohexene.

Substituted derivatives of any of the terpenes or cycloalkenes mentioned above may also be used. Typically 1, 2, 3 or more substituents are present. Any combination of the following substituents may be present. The substituent is typically a halogen atom or an alkyl or alkenyl group, which generally has 1 to 6 carbons, the substituent optionally being substituted with one or more halogens. It is generally not phenylcyclohexene. Indeed the presence of aromatic, such as phenyl, rings is generally avoided for all the substrates used in the invention.

The substituent typically has the formula $C_nH_kX_m$, wherein X is the halogen, n is 1, 2, 3 or more, m is 1, 2, 3, 4 or more and k is an integer which has an appropriate value so that the valencies of the substituent $C_nH_kX_m$ are satisfied. For an alkyl substituent k+m=2n+1. Typically k is 1, 2, 3, 4 or more, or may be 0, i.e. the substituent is a perhaloalkyl group. The halogen is typically fluorine, chlorine or bromine.

The substituent may also comprise 1, 2 or more oxygen atoms and for example may be an alcohol, aldehyde, ketone or epoxide group.

The oxidation causes the formation of a C—O bond in the compound, generally as the hydroxide from the oxidation of a carbon-hydrogen bond, but an epoxide may be formed from the oxidation of a C=C bond. The oxidation may thus introduce a hydroxy, aldehyde, ketone or epoxide group. Alternatively the oxidation may cause the further oxidation of an oxygen containing group, such as converting a hydroxy group into an aldehyde or ketone group. 1, 2 or more carbon atoms may be attacked in the same substrate molecule.

The oxidation typically gives rise to 1, 2 or more oxidation products. These different products may result from different carbon atoms being attacked and/or from different degrees of oxidation occurring at a given carbon atom.

The oxidation may occur on either a ring carbon atom or a substituent carbon atom or both. At least the initial oxidation will involve attack of a C—H bond which may be activated or non-activated or attack at a carbon—carbon double bond (typically giving an epoxide). Generally an activated C—H bond is where the carbon atom is in a benzylic or allyl position. Aromatic rings and olefinic double bonds activate C—H bonds to attack by stabilising the radical intermediate or any build-up of charge generated during the reaction pathway. The carbon of the C—H bond may be a primary, secondary or tertiary carbon.

The oxidation typically preserves stereoisomerism. Thus when the substrate consists of a single stereoisomer the product typically consists of a single corresponding stereoisomer, or can contain a preponderance of the corresponding stereoisomer.

The enzyme used in the process is generally a P450 enzyme, typically of eukaryotic or prokaryotic origin. The enzyme is generally of bacterial, fungal, yeast, plant or animal origin, and thus may be from a bacterium of the genus *Pseudomonas*. The enzyme is typically a monooxygenase. The non-mutant form of the enzyme may or may not be able to oxidize terpenes and/or cycloalkenes.

The mutations discussed herein are generally introduced into the enzyme by using methods known in the art, such as site directed mutagenesis of the enzyme, PCR and gene shuffling methods or by the use of multiple mutagenic oligonucleotides in cycles of site-directed mutagenesis. Thus the mutations may be introduced in a directed or random manner. The mutagenesis method thus produces one or more polynucleotides encoding one or more different mutants. Typically a library of mutant oligonucleotides is produced which can be used to produce a library of mutant enzymes.

An amino acid 'in the active site' is one which lines or defines the site in which the substrate is bound during catalysis or one which lines or defines a site through which the substrate must pass before reaching the catalytic site. Therefore such an amino acid typically interacts with the substrate during entry to the catalytic site or during catalysis. Such an interaction typically occurs through an electrostatic interaction (between charged or polar groups), hydrophobic interaction, hydrogen bonding or van der Waals forces.

The amino acids in the active site can be identified by routine methods to those skilled in the art. These methods include labelling studies in which the enzyme is allowed to bind a substrate which modifies ('labels') amino acids which contact the substrate. Alternatively the crystal structure of the enzyme with bound substrate can be obtained in order to deduce the amino acids in the active site.

The enzyme may have 1, 2, 3, 4, 5 to 10, 10 to 20 or more other mutations, such as substitutions, insertions or deletions. The other mutations may be in the active site or outside the active site. Typically the mutations are in the 'second sphere' residues which affect or contact the position or orientation of one or more of the amino acids in the active site. The insertion is typically at the N and/or C terminal and thus the enzyme may be part of a fusion protein. The deletion typically comprises the deletion of amino acids which are not involved in catalysis, such as those outside the active site (thus the enzyme is a mutated fragment of a naturally occurring enzyme). The enzyme may thus comprise only those amino acids which are required for oxidation activity.

The other mutation in the active site typically alters the position and/or conformation of the substrate when it is bound in the active site. The mutation may make the site on the substrate which is to be oxidized more accessible to the haem group. Thus the mutation may be a substitution to an amino acid which has a smaller or larger, or more or less polar, side chain.

The other mutations typically increase the stability of the protein, or make it easier to purify the protein. They typically prevent the dimerisation of the protein, typically by removing cysteine residues from the protein (e.g. by substitution of cysteine at position 334 of $P450_{cam}$, or at an equivalent position in a homologue, preferably to alanine). They typically allow the protein to be prepared in soluble form, for example by the introduction of deletions or a poly-histidine tag, or by mutation of the N-terminal membrane anchoring sequence. The mutations typically inhibit protein oligomerisation, such as oligomerisation arising from contacts between hydrophobic patches on protein surfaces.

Thus the mutant enzyme is typically at least 70% homologous to a naturally occurring haem-containing enzyme on the basis of amino acid identity.

Any of the homologous proteins (i.e. described as being homologous to another protein) mentioned herein are typically at least 70% homologous to the relevant protein or at least 80 or 90% and more preferably at least 95%, 97% or 99% homologous thereto over at least 20, preferably at least 30, for instance at least 40, 60 or 100 or more contiguous amino acids. The contiguous amino acids may include the active site. This homology may alternatively be measured not over contiguous amino acids but over only the amino acids in the active site.

Homology can be measured using known methods. For example the UWGCG Package provides the BESTFIT program which can be used to calculate homology (for example used on its default settings) (Devereux et al (1984) *Nucleic Acids Research* 12, p 387–395). The PILEUP and BLAST algorithms can be used to calculate homology or line up sequences (typically on their default settings), for example as described in Altschul S. F. (1993) J Mol Evol 36:290–300; Altschul, S, F et al (1990) J Mol Biol 215:403–10.

Software for performing BLAST analyses is publicly available through the National Center for Biotechnology Information. This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quality X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) Proc. Natl. Acad. Sci. USA 89: 10915–10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci.* USA 90: 5873–5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

Typically the homologous protein differs from the relevant protein by at least 1, 2, 5 or 10 mutations (substitutions, insertions or deletions) when compared to all of the protein or over any of the lengths of contiguous amino acids mentioned above.

The enzyme used in the process is preferably a mutant of $P450_{cam}$ (such as mutant of the sequence shown in table 7; nucleic acid sequence is SEQ ID NO:1, amino acid sequence is SEQ ID NO:20) or a mutant of a naturally occurring homologue of $P450_{cam}$, typically of $P450_{BM-3}$ from *Bacillus megaterium* (such as a mutant of the sequence shown in table 8; SEQ ID NO:2), $P450_{terp}$ from *Pseudomonas* sp, and $P450_{eryF}$ from *Saccharopollyspora erythraea*, and also P450 105 D1 (CYP105) from *Streptomyces griseus* strains. Note that the amino acid numbering shown in table 8 for $P450_{BM-3}$ (SEQ ID NO:21) does not correspond to the numbering used in the description to denote mutations in this enzyme. The sequence shown in table 8 contains an additional amino acid at the N terminal. This is normally cleaved in vivo. Therefore each amino acid number shown in the table is always one more than the number used in the conventional numbering (as used in the description).

The naturally occurring homologue of $P450_{cam}$ (e.g. of $P450_{BM-3}$) may have substantially the same activity as $P450_{cam}$ or $P450_{BM-3}$. The homologue may be a species homologue or an allelic variant of $P450_{cam}$ from *Pseudomonas putida* or of $P450_{BM-3}$. The amino acids in the active site of the homologue may be the same as in the active site of $P450_{cam}$ or of $P450_{BM-3}$. Typically the amino acid at the equivalent position to 96 in $P450_{cam}$ is a tyrosine in the homologue.

The mutant of $P450_{cam}$ or of a homologue of $P450_{cam}$ is typically one in which amino acid 96, or the equivalent amino acid in a homologue, has been changed to an amino acid with a less polar side chain. In the case where the homologue is $P450_{BM-3}$ the mutant typically has a substitution (to a less polar amino acid) at 47 and/or 51 and/or 42 and/or 75 and/or 354 and/or 264 and/or 263 and/or 181 and typically does not have a mutation at the equivalent site to 96 of $P450_{cam}$ (preferred mutants of $P450_{BM-3}$ have at least mutations at 47 and 51, or at the equivalent sites in homologues).

Thus typically the substitution is to an amino acid which is above the original amino acid in Table 3, such as the preferred mutations shown in Table 4 and Table 5.

The 'equivalent' side chain in the homologue is one at the homologous position. This can be deduced by lining up the $P450_{cam}$ or $P450_{BM-3}$ sequence and the sequence of the homologue based on the homology between the two sequences. The PILEUP and BLAST algorithms can be used to line up the sequences. The equivalent amino acid will generally be in a similar place in the active site of the homologue as any of the specific amino acids discussed herein, such as amino acid 96 in $P450_{cam}$.

The discussion below provides examples of the positions at which substitutions may be made in $P450_{cam}$ and $P450_{BM-3}$. The same substitutions may be made at equivalent positions in the homologues. Standard nomenclature is used to denote the mutations. The letter of the amino acid present in the natural form is followed by the position, followed by the amino acid in the mutant (these positions can be correlated to the numbering shown in tables 7 and 8 with the proviso discussed above with regard to table 8 amino acid numbering). To denote multiple mutations in the same protein each mutation is listed separated by hyphens. The mutations discussed below using this nomenclature specify the natural amino acid in $P450_{cam}$ or $P450_{BM-3}$ but it is to be understood that the (same) mutation could be made to a homologue which has a different amino acid at the equivalent position.

An additional mutation is typically an amino acid substitution at amino acid 87, 98, 101, 185, 244, 247, 248, 296, 395, 396 of $P450_{cam}$ (or a combination of these, for example as shown in table 4).

The following combinations of substitutions are preferred for $P450_{cam}$:

(i) Substitution at position 87 to amino acids of different side-chain volume, such as substitutions (typically of F) to A, L, I and W, combined with substitutions at position 96 to amino acids of different side-chain volume such as (typically Y to) A, L, F, and W. These combinations alter the space available in the upper part of the substrate pocket compared to the wild-type enzyme, for example, from Y96W-F87W (little space) to Y96A-F87A (more space), as well as the location of the space, for example from one side in Y96F-F87A to the other in Y96A-F87W.

(ii) Substitution at position 96 to F combined with substitutions at positions 185 and 395. Both T185 and I395 are at the upper part of the substrate pocket, and substitution with A creates more space while substitution with F will reduce the space available and push the substrate close to the haem.

(iii) Substitutions at position 96 to A, L, F, and W combined with substitutions at residues closer to the haem including at 101, 244, 247, 295, 296 and 396 to A, L, F, or W. These combinations will create or reduce space in the region of the different side-chains to offer different binding orientations to substrates of different sizes. For example, the combinations Y96W-L244A and Y96L-V247W will offer very different substrate pockets for the binding of R-limonene.

(iv) Triple substitutions at combinations of positions 87, 96, 244, 247, 295, 296, 395 and 396 with combinations of A, L, F, and W. The aim is to vary the size and shape of the hydrophobic substrate binding pocket. For example, the Y96A-F87A-L244A combination creates more space compared to the Y96F-F87W-V396L combination, thus allowing larger terpenes to bind to the former while restricting the available binding orientations of smaller terpenes in the latter. The combinations Y96F-F87W-V247L and Y96F-F87W-V295I have comparable substrate pocket volumes, but the locations of the space available for substrate binding are very different. The combination Y96F-F87L-V247A has a slightly larger side-chain volume at the 96 position than the combination Y96L-F87L-V247A, but the L side-chain at the 96 position is much more flexible and the substrate binding orientations will be different for the two triple mutants.

(v) The mutants with four or five substitutions were designed with similar principles of manipulating the substrate volume, the different flexibility of various side-chains, and the location of the space available in the substrate pocket for terpene binding so as to effect changes in selectivity of substrate oxidation.

The invention also provides the mutant of $P450_{cam}$ or a mutant of a homologue of $P450_{cam}$ (such as $P450_{BM-3}$) as discussed above, excluding mutants of $P450_{cam}$ which only have the mutations:

F87A-Y96G-F193A, F87A-Y96G-F193A-C334A or T101M-T185F-V247M.

The mutant enzyme may be in a substantially isolated form and/or a substantially purified form, in which case it will generally comprise (e.g. about or at least) 90%, such as (e.g. about or at least) 95%, 98% or 99% of the protein in the preparation.

The invention also provides a polynucleotide which comprises a sequence which encodes the mutant enzyme of the invention. The polynucleotide is typically DNA or RNA, and may be single or double stranded. The polynucleotide may be able to hybridise with a polynucleotide encoding the naturally occurring form of any mutant discussed herein (each the polynucleotide shown in table 7 or 8). It typically hybridises with the relevant polynucleotide at a level significantly above background. The signal level generated by the interaction is typically at least 10 fold, preferably at least 100 fold, as intense as 'background' hybridisation. The intensity of interaction may be measured, for example, by radiolabelling the probe, e.g. with $^{32}P$. Selective hybridisation is typically achieved using conditions of medium to high stringency (for example 0.03M sodium chloride and 0.03M sodium citrate at from about 50° C. to about 60° C.).

Polynucleotides of the invention can be incorporated into a recombinant replicable vector. The vector may be used to replicate the nucleic acid in a compatible host cell. Thus one method of making polynucleotides of the invention comprises introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

Such vectors may be transformed into a suitable host cell to provide for expression of the mutant enzyme.

The vectors may be, for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell.

Promoters and other expression regulation signals may be selected to be compatible with the host cell for which the expression vector is designed. For example, E. Coli promoters include lac, tac, trc, trp and T7 promoters, and yeast promoters include S. cerevisiae GAL4 and ADH promoters, S. pombe nmt1 and adh promoters. Mammalian promoters include the metallothionein promoter which can be induced in response to heavy metals such as cadmium. The expression vectors are possible for use in insect or mammalian cells. For use in insect cells, strong baculovirus promoters such as the polyhedrin promoter are preferred. For expression in mammalian cells, strong viral promoters such as the SV40 large T antigen promoter, a CMV promoter or an adenovirus promoter may also be used. All these promoters are readily available in the art.

Expression vectors of the invention are typically introduced into host cells using conventional techniques including calcium phosphate precipitation, DEAE-dextran transfection, or electroporation.

The expression vector may contain a selectable marker and/or such a selectable marker may be co-transfected with the expression vector and stable transfected cells may be selected.

Suitable cells include cells in which the abovementioned vectors may be expressed. Such cells may be prokaryotic or eukaryotic. These include microbial cells typically bacteria such as E. coli, preferably the strains $DH_{5\alpha}$, JM109, NM522 and BL21DE3 or Pseudomonas, typically putida, mammalian cells such as CHO cells, COS7 cells or HeLa cells, insect cells or yeast such as Saccharomyces. Baculovirus or vaccinia expression systems may be used.

Cell culture can take place under standard conditions. Generally the cells are cultured in the presence of assimible carbon and nitrogen sources. Commercially available culture media for cell culture are widely available and can be used in accordance with manufacturers instructions.

Typically the process of the invention is carried out in vitro, such as in a cell free system. The process may be carried out in vivo in a cell.

Typically, in addition to the enzyme (a) and the substrate the process of the invention is carried out in the presence of an electron transfer reductase (b), an electron transfer redoxin (c), cofactor for the enzyme and an oxygen donor. In this system the flow of electrons is typically: cofactor→(b)→(c)→(a). However particular enzymes do not require the presence of an electron reductase and electron transfer redoxin, such as $P450_{BM-3}$. Although the following discussion is particularly directed to enzymes which do require a reductase or redoxin, it is applicable to enzymes which do not require these (for example the various concentrations, conditions and rates are suitable for these enzymes).

For enzymes which do require a reductase and redoxin (b) is generally an electron transfer reductase which is able to mediate the transfer of electrons from the cofactor to (c), such as a naturally occurring reductase or a protein which has homology with a naturally occurring reductase, such as at least 70% homology; or a fragment of the reductase or homologue. Thus (b) may be derived from any of the organisms listed above from which the haem-containing enzyme may be derived. (b) is typically a flavin dependent reductase, such as putidaredoxin reductase.

(c) is generally an electron transfer redoxin which is able to mediate the transfer of electrons from the cofactor to (a) via (b). (c) is typically a naturally occurring electron transfer redoxin or a protein which has homology with a naturally occurring electron transfer redoxin, such as at least 70% homology; or a fragment of the redoxin or homologue. Thus (c) may be derived from any of the organisms listed above from which the haem-containing enzyme may be derived. (c) is typically a two-iron/two sulphur redoxin, such as putidaredoxin.

The cofactor is any compound capable of donating an electron to (b), such as NADH. The oxygen donor is any compound capable of donating oxygen to (a), such as dioxygen.

In the process the concentration of (a), (b) or (c) is typically from $10^{-8}$ to $10^{-2}M$, preferably from $10^{-6}$ to $10^{-4}M$. Typically the ratio of concentrations of (a): (b) and/or (a): (c) is from 0.1:01 to 1:10, preferably from 1:0.5 to 1:2, or from 1:0.8 to 1:1.2. Generally the process is carried out at a temperature and/or pH at which the enzyme is functional, such as when the enzyme has at least 20%, 50%, 80% or more of peak activity. Typically the pH is from 3 to 11, such as 5 to 9 or 6 to 8, preferably 7 to 7.8 or 7.4. Typically the temperature is 15 to 90° C., such as 25 to 75° C. or 30 to 60° C. In one embodiment the process is carried out in the presence of a substance able to remove hydrogen peroxide by-product (e.g. a catalase).

Alternatively the process of the invention could be carried out in the presence of the enzyme, substrate and an oxygen atom donor, such as hydrogen peroxide or t-butylhydroperoxide. Thus, the process could be carried out using the peroxide shunt.

Typically in the process at least 20 turnovers/min occur, such as at least 50, 100, 200, 300, 500 or more turnovers (turnover is measured as nanomoles of product formed per nanomole of enzyme).

The invention also provides several types of cells. The first type expresses an enzyme which can be used in the process which in its naturally occurring form has an electron transfer reductase domain; or expresses
(a) the mutant haem-containing enzyme which is used in the process of the invention;
(b) an electron transfer reductase; and
(c) an electron transfer redoxin.

The second type of cell expresses:
(a) (i) $P450_{cam}$ or a fragment thereof; or
(ii) a naturally occurring homologue of $P450_{cam}$ or a fragment thereof; or
(iii) a mutant of $P450_{cam}$; or
(iii) a polypeptide which has at least 70% amino acid homology with (i) or (ii) and optionally has any of the combination of mutations discussed herein; and
(b) an electron transfer reductase; and
(c) an electron transfer redoxin:
excluding an E. Coli DH5* cell in which the only mutants of $P450_{cam}$ which are expressed are amongst the following:
$H_2N-P450_{cam}$-TDGTSST (SEQ ID NO:3)-putidaredoxin reductase-TDGASSS (SEQ ID NO:4)-putidaredoxin-COOH,
$H_2N-P450_{cam}$-TDGTRPGPGPGPGPSST (SEQ ID NO:5)-putidaredoxin reductase-TDGASSS-putidaredoxin-COOH,
$H_2N-P450_{cam}$-TDGTRPGPGPGPGPGPSST (SEQ ID NO:6)-putidaredoxin reductase-TDGASSS-putidaredoxin-COOH,
$H_2N$-putidaredoxin reductases-TDGASSS-putidaredoxin-PLEL (SEQ ID NO:7)-$P450_{cam}$-COOH.

However it is understood that the excluded E. Coli DH5α cells can be used to produce the libraries discussed below.

A preferred cell (second type) is a cell which expresses:
(a) (i) $P450_{BM-3}$, or a fragment thereof; or
(ii) a naturally occurring homologue of $P450_{BM-3}$ or a fragment thereof; or
(iii) a mutant $P450_{BM-3}$, or a mutant homologue of thereof.

The cell provided by the invention is typically a cell from the species mentioned above in which the nucleotide of the invention can be expressed. The cell may be a mutator cell. Such a cell is generally deficient in one or more of the primary DNA repair pathways (such as E. Coli pathways mutS, mutD or mutT, or their equivalents in another organism), and thus has a high mutation rate. Simply culturing such cell leads to the DNA encoding (a) to become mutated. The cell may be of E. Coli XL1 Red mutator strain.

The cell of the invention may be in a substantially isolated form and/or substantially purified form, in which case it will generally comprise (e.g. at least or about) 90%, such as (e.g. at least or about) 95%, 98% or 99% of the cells or the mass (normally measured in terms of dry mass) of the preparation.

The cell may be one which does not naturally express (a), (b) or (c). The cell be one in which (a), (b) or (c) are expressed at a higher level than in the naturally occurring cell. (a) may originate from the same organism as (b) or (c).

In the cell (a), (b) and (c) may be expressed from the same vector, or may be expressed from different vectors. They may be expressed as three different polypeptides. Alternatively they may be expressed in the form of fusion proteins. Typically components (a), (b) and (c) are all present in the same fusion protein. Alternatively only two of the components, preferably (b) and (c), may be present in the fusion protein. Typically the components are contiguous in the fusion protein and there is no linker peptide present.

Alternatively a linker may be present between the components. The linker generally comprises amino acids that do not have bulky side chains and therefore do not obstruct the folding of the protein subunits. Preferably the amino acids in the linker are uncharged. Preferred amino acids in the linker are glycine, serine, alanine or threonine. In one embodiment the linker comprises the sequence N-Thr-Asp-Gly-Gly-Ser-Ser-Ser-C (SEQ ID NO:8). The linker is typically from at least 5 amino acids long, such as at least 10, 30 or 50 or more amino acids long.

The first type of cell may be obtained by transforming or transfecting a host cell with a polynucleotide or vector of the invention.

The mutant enzyme of the invention may be prepared by a process comprising cultivating the first type of cell under conditions to provide for expression of the said mutant enzyme, and optionally recovering the expressed mutant enzyme.

The process of the invention may be carried out in the first type of cell of the invention or in the second type of cell if it is able to oxidize the substrate, or a medium containing it. Generally such a process comprises providing the substrate in the cell, allowing the substrate to be oxidized in the process of the invention, and optionally obtaining the oxidation product therefrom, e.g. by extraction. The substrate is typically provided in the cell by adding the substrate to the outside of the cell and allowing it to enter the cell. Alternatively the substrate could be synthesized in the cell from a precursor.

The invention also provides a process for making a library of mutants of $P450_{cam}$ or mutants of a homologue of $P450_{cam}$ comprising contacting the second type of cell with a mutagen and/or when the cell is a mutator cell culturing the cell in conditions in which mutants are produced. The mutagen may be contacted with the cell prior to or during culturing of the cell. Thus the mutagen may be present during replication of the cell or replication of the genome of the cell.

The mutagen generally causes random mutations in the polynucleotide sequence which encodes (a). The mutagen is typically a chemical mutagen, such as nitrosomethyguanidine, methyl- or ethylmethane sulphonic acid, nitrite, hydroxylamine, DNA base analogues, and acridine dyes, such as proflavin. It is typically electromagnetic radiation, such as ultra-violet radiation at 260 nm (absorption maximum of DNA) and X-rays. It is typically ionising radiation.

Typically the library will be in the form of cells which are derived from cells of the invention by mutagenesis and which cells comprise the mutant enzymes. Generally each cell will express only one particular mutant enzyme. The library typically comprises at least 500 mutants, such as at least 1,000 or 5,000 mutants, preferably at least 10,000 different mutants.

The library typically comprises a random population of mutants. The library may undergo one or more rounds of selection whilst being produced and therefore may not comprise a random population. Between rounds of selection the cells in the library may be allowed to replicate, and they may also be contacted with a mutagen.

A mutant can be selected from the library based on a particular property of the mutant. The property may comprise one or more of the following characteristics:

(i) the ability to oxidize a particular substrate; optionally to a particular oxidation product or to a product with a particular activity.

(ii) the ability to carry out the oxidation of substrate at an increased rate, (iii) a reduced oxidation activity towards a particular substrate, (iv) a reduction in the production of a particular substrate.

Typically the activity of the product in (i) is blocking the action of an agent which is lethal to the cells of the library. This can be selected by growing the library in the presence of the agent. The agent is typically expressed within the cells of the library.

The activity may be the binding of the product to a particular substance, such a protein. The substance is typically present in the cell of the library, and/or is typically a disease-causing or therapeutic target. An indicator which binds the substance is typically used to detect binding of the product to the substance. In one embodiment the indicator is able to bind the substance and has a property which changes upon binding, e.g. a colour change. Product which displaces the indicator from the substance can thus be detected by measuring changed in the property.

The invention also provides a method of making a library of oxidation products comprising providing a substrate to the library of mutant enzymes and allowing oxidation of the substrate.

Products produced in the process of the invention, or identified, selected, made or designed using the library could be used in therapy or diagnosis. Thus the invention provides a method of treating a host suffering from a disease, which method comprises administering to the host a therapeutically effective amount of the product. The condition of a patient suffering from the disease and in need of the product can therefore be improved by administration of the product. The product can also be given as a prophylactic, typically to a host which is at risk from or susceptible to the disease.

The invention provides the product for use in a method of treatment of the human or animal body by therapy. The invention also provides the product for use in a diagnostic method practiced on the human or animal body. The invention also provides use of the product in the manufacture of a medicament to treat a disease.

The formulation of the product for use in preventing or treating infection by an organism will depend upon factors such as the nature of the product identified, whether a pharmaceutical or veterinary use is intended, etc. In order to be administered to a patient, the compound will be provided in the form of a pharmaceutical composition containing the product and a pharmaceutically acceptable carrier or diluent. Suitable carriers and diluents include isotonic saline solutions, for example phosphate-buffered saline. Typical oral dosage compositions include tablets, capsules, liquid solutions and liquid suspensions. For example it may be formulated for parenteral, intravenous, intramuscular, subcutaneous, transdermal or oral administration.

The dose of product may be determined according to various parameters, especially according to the substance used; the age, weight and condition of the patient to be treated; the route of administration; and the required regimen. A physician will be able to determine the required route of administration and dosage for any particular patient. A suitable dose may however be from 0.1 to 100 mg/kg body weight such as 1 to 40 mg/kg body weight, for example, to be taken from 1 to 3 times daily.

The invention is illustrated by the accompanying drawings which show the gas chromatography results for various oxidation reactions. In the drawings unless stated otherwise the y-axis shows mVolts and the x-axis shows Time (in minutes).

IN THE DRAWINGS

FIG. 1 shows the oxidation of camphor by the C334A mutant of P450$_{cam}$ (expressed from plasmid SGB++). Lines A, B, C, D and E represent camphor turnover at 2, 10, 20, 40 and 100 minutes. The 5.28 peaks is camphor, 11.82 is 5-exo-hydroxycamphor, 7.45 is 5-ketocamphor and the 16.07 peak is the internal standard.

EXAMPLE 1

Figure 1:
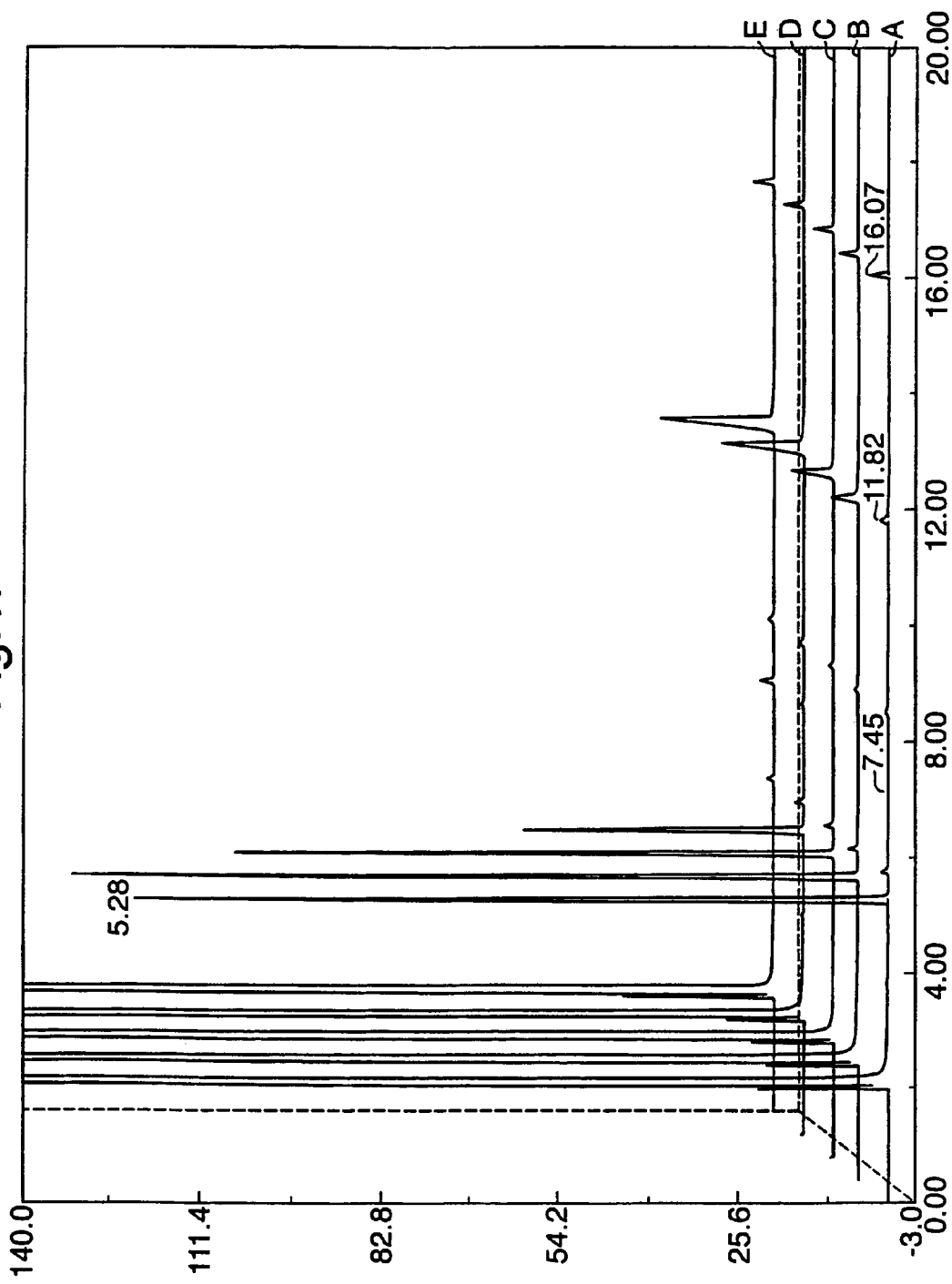
Figure 2:
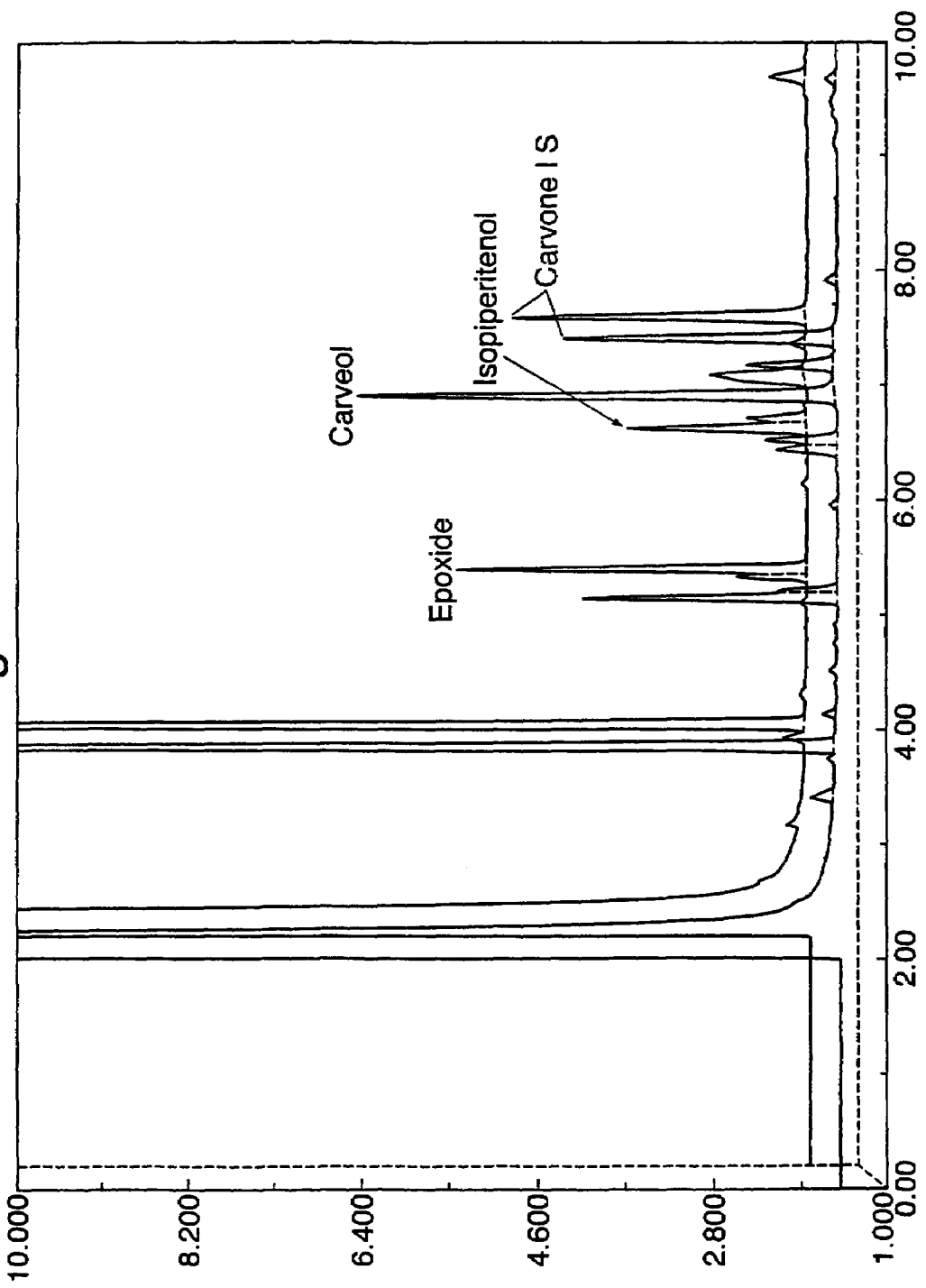
FIG. 2 shows R- and S-limonene with wild type P450$_{BM-3}$.
Figure 3:
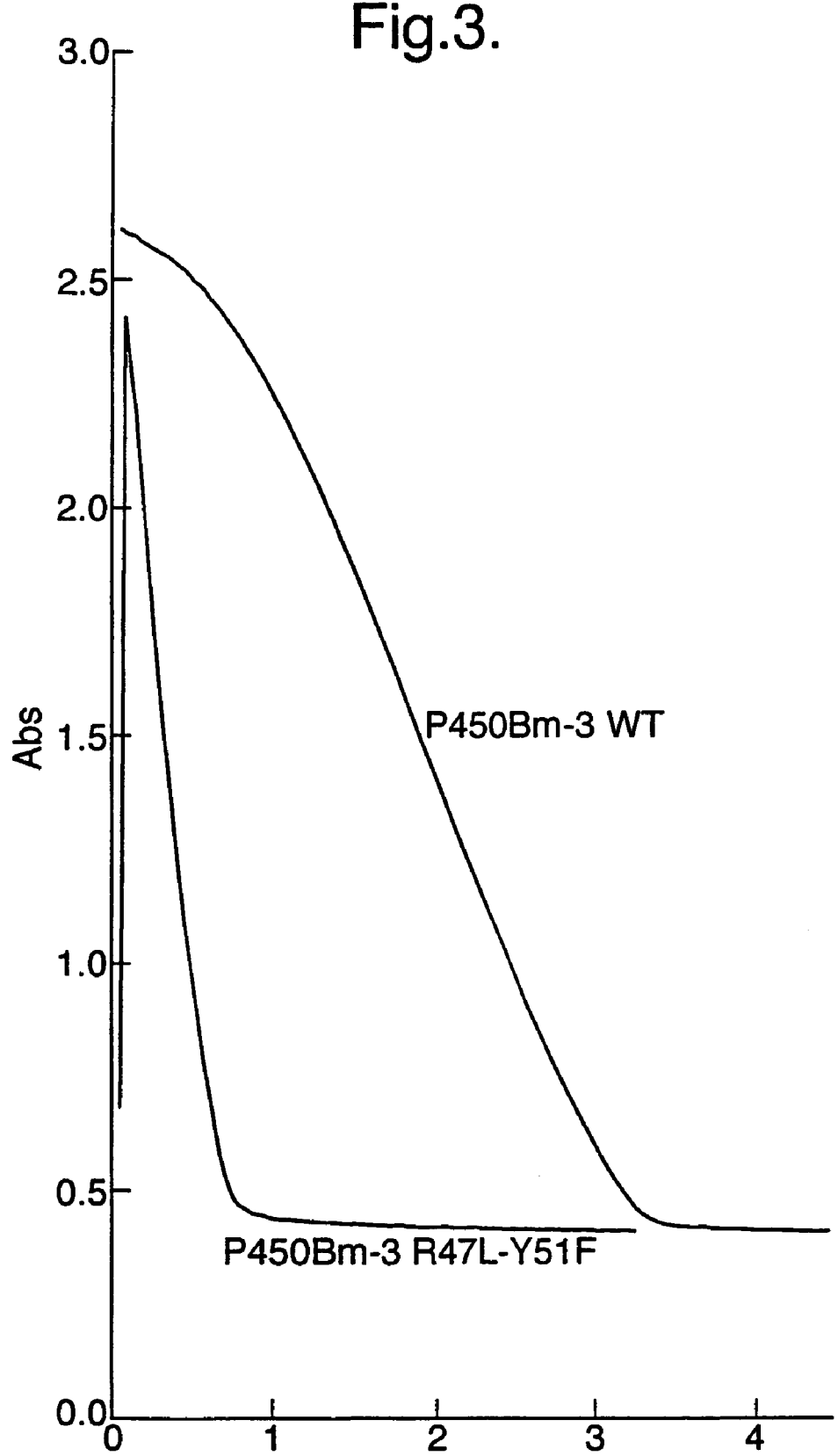
FIG. 3 shows NADH consumption by wild type and mutant P450$_{BM-3}$.
Figure 4:
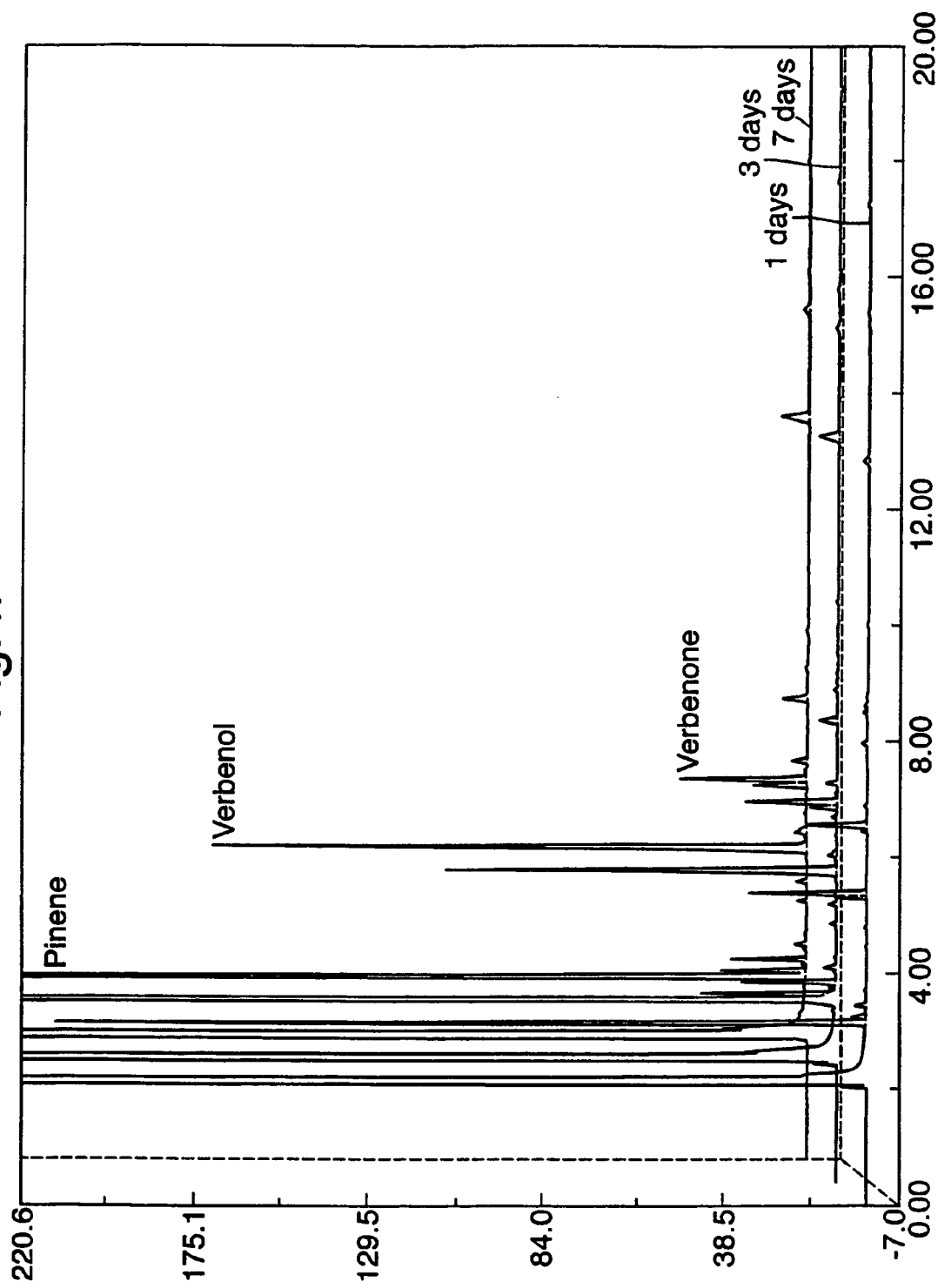
FIG. 4 shows the whole cell E. coli oxidation of α-pinene by the Y96F-F87W-V247L mutant expressed by plasmid pCWSGB+.

Expression of Mutants for In Vitro Work.

The P450$_{cam}$ enzymes were expressed using the vector pRH1091 (Baldwin, J. E., Blackburn, J. M., Heath, R. J., and Sutherland, J. D. *Bioorg. Med. Chem. Letts.*, 1992, 2, 663–668.) which utilised the trc promoter (a fusion of the trp and lac promoters). This vector incorporates a strong ribosome binding site (RBS) and the gene to be expressed is cloned using an Nde I site on the 5' end of the gene. We used Hind III as the cloning site at the 3' end of the camC gene. The procedure for protein expression is as follows: Cells are grown at 30° C. until the OD$_{600\ nm}$ reaches 1.0–1.2, the temperature is increased to 37° C. and camphor added as a 1 M stock in ethanol to a final concentration of 1 mM. The culture is allowed to incubate at 37° C. for another 6 hours. The P450$_{cam}$ protein is expressed to high levels in the cytoplasm and the cells take on a red to orange-red colour.

We have also prepared a variant of pRH1091 (by PCR) which has a extra Xba I site between the RBS and the Nde I site. This is important because Nde I is not unique in M13, and this restriction site is also present in the reductase gene as well as the backbone of the pGLW11 vector used for the in vivo system. Xba I is unique in the polylinker region of M13, but absent in the genes of all three proteins in the P450$_{cam}$ system and in the expression vectors. It therefore allows the camC gene to be moved between the mutagenic and expression vectors.

The P450$_{BM-3}$ enzyme from *Bacillus megaterium* was expressed using either the pGLW11 or pCW vectors. The recombinant plasmid with the P450$_{BM-3}$ gene inserted into either of these vectors were transformed into E. coli strain DH5α and grown under ampicillin selection. A single colony was then grown at 30° C. in LB media supplemented with ampicillin until the OD at 600 nm reached ca. 1, and protein expression was induced by adding IPTG from a 1 M stock to a final concentration of 1 mM. After 6–8 h, cells were harvested by centrifugation and the expression levels were high, as indicated by an orange-red coloration of the cells.

How the Mutants were Made.

Oligonucleotide-directed site-specific mutagenesis was carried out by the Kunkel method (Kunkel, T. A. *Proc. Natl. Acad. Sci. USA* 1985, 82, 488–492) using the Bio-Rad Mutagen kit and by PCR using the QuikChange kit from Stratagene. The recommended procedure for the Kunkel method is summarised as follows. An M13 mp19 subclone of the camC gene encoding $P450_{cam}$ was propagated in the *E. coli* strain CJ236. This strain has the dut⁻ung⁻ phenotype and thus will tolerate the inclusion of uracil in place of thymine in DNA molecules. After three cycles of infection, uracil-containing single stranded (USS) M13 DNA was readily isolated by phenol extraction of mature M13 phage particles excreted into the growth medium. The mutagenic oligonucloetide (or oligonucleotides) were phosphorylated with T4 polynucleotide kinase and then annealed to the USS template. The four nucleotides, DNA polymerase, DNA ligase, ATP and other chemical components were added and the second strand was synthesised in vitro. The double stranded form thus obtained was transformed into the dut+ ung+ *E. coli* strain MV1190, which should degrade the uracil-containing template strand and propagate the mutant strand synthesised in vitro. Plaques were picked and phages of possible mutants grown in *E. coli* strains MV1190 or TG1. The single-stranded DNA from these were sequenced to determine whether the mutagenesis reaction was successful. The mutagenic efficiency was 50–80%. The mutant camC gene is excised from the M13 subclone by restriction digest with Nde I and Hind III, and the fragment of appropriate size is ligated to the backbone of the expression vector prepared by a similar Nde I/Hind III digest.

The QuikChange kit relies on the property of the Dpn I restriction enzyme which selectively cleaves methylated DNA. The mutation is introduced by PCT using double stranded plasmid DNA, and hence no single stranded template preparations are necessary. The PCR reaction is carried out with two oligonucleotides, one of which binds to the coding strand and the other to the sense strand. Each oligonucleotide contains a short stretch of polynucleotide complementary to either side of the mutation site. After in vitro synthesis by PCR using non-methylated dNTP's, plasmid DNA with overlapping nicks in each strand were digested with Dpn I to remove the starting template selectively—plasmid DNA isolated from most *E. coli* strains contain methylated bases but the newly synthesised DNA do not have methylated bases. After the digest the DNA is transformed into supercompetent *E. coli* XL1 Blue cells and propagated. The plasmid DNA from potential mutants which grow on agar plates under antibiotic selection were isolated and sequenced to confirm mutagenesis. The cells can then be used for protein expression once the entire sequence of the new mutant was confirmed to ensure that there were no spurious mutations.

Multiple mutants were prepared either by further mutagenesis, also by the Kunkel method, or where the location of the sites in the sequence permits, simple cloning steps. There are two unique restriction sites within the camC gene which are absent from the expression vector. One is Sph I which spans residues 121–123, and the other is Sal I which spans residues 338 and 339. Therefore, all mutations at, for example, residues 87, 96, 98, and 101 are readily combined with mutations at higher number residues by ligating appropriate fragments from restriction digests of mutant camC genes with Nde I/Sph I and Sph I/Hind III and the backbone fragment from a Nde I/Sph I digest of the expression vector. Mutations at, for example, 395 and 396 can be similarly incorporated by digests in which Sph I is replaced with Sal I.

The rationale for introducing the unique Xba I site is now clear: many mutants with multiple mutations were prepared by the cloning procedure above. Without the Xba I site it would be impossible to clone the gene for these multiple mutants from the expression vector back into M13 for further rounds of mutagenesis. Of course these problems could be overcome by doing mutagenesis by PCR, for example.

EXAMPLE 2

Substrate oxidation protocol: in vitro reactions

| Component | Final concentration |
| --- | --- |
| $P450_{cam}$ enzyme | 1 µM |
| Putidaredoxin | 10 µM |
| Putidaredoxin reductase | 1 µM |
| Bovine liver catalase | 20 µg/ml |
| KCl | 200 mM |
| Substrate | Typically 1 mM |
| NADH | 250–400 µM |

50 mM Tris-HCl buffer pH 7.4 is added to make up the volume.

Temperature controlled at 30° C., optional.

The NADH turnover rate could be determined by monitoring the absorbance at 340 nm with time.

Catalase does not catalyse the substrate oxidation reactions but rather it is present to remove any hydrogen peroxide by-product which could otherwise denature the $P450_{cam}$.

The method can be increased in scale to, for example, 20 ml total incubation volume to allow purification of sufficient products by HPLC for spectroscopic characterisation. Fresh substrate (1 mM) and NADH (1–2 mM) are added periodically, such as every 20 minutes in a total reaction time of, typically, 3 hours.

EXAMPLE 3

The In Vivo System

The in vivo systems were expressed using the vector pGLW11, a derivative of the plasmid pKK223 (Brosius, J. and Holy, A. *Proc. Natl. Acad. Sci. USA*, 1984, 81, 6929–6933). Expression is directed by the tac promoter and the vector incorporates a gene conferring resistance to the antibiotic ampicillin.

Two systems were constructed. The first one expressed the electron transfer proteins putidaredoxin reductase (camA gene) and putidaredoxin (camB gene) as a fusion protein with a seven amino acid peptide linker, and the $P450_{cam}$ enzyme (camC gene) was expressed by the same vector but it was not fused to the electron proteins. The second system expressed the three proteins as separate entities in the *E. Coli* host. Both systems were catalytically competent for substrate oxidation in vivo.

The general strategy was as follows. The genes for the three proteins were cloned using Eco RI and Hind III as flanking sites, with Eco RI at the 5' end. For both in vivo systems there are restriction sites between the genes, including between the reductase and redoxin genes in the fusion construct. These restriction sites were introduced by PCR, as detailed below. The first task, however, was to carry out a silent mutation to remove the Hind III site within the camA gene for the reductase. The AAGCTT Hind III recognition sequence in the camA gene was changed to AAGCCT, which is a silent mutation because GCT and GCC both encode alanine. The gene was completely sequenced to ensure that there were no spurious mutations.

1. The Fusion Protein System

1.a Manipulation of the CamA Gene by PCR

For the camA gene the primer below (SEQ ID NO:9) was used at the 5' end of the gene to introduce the Eco RI cloning site and to change the first codon from GTG to the strong start codon ATG.

```
5'- GAG ATT AAG AAT TCA TAA ACA CAT GGG AGT GCG TGC CAT ATG AAC GCA
AAC
          Eco RI         RBS         **camA
```

At the 3' end of camA the primer was designed such that 15 bases are complementary to nucleotide sequence of the last five amino acid residues of camA. The stop codon immediately after the GCC codon for the last amino acid was removed, and then part of a seven amino acid linker (Thr Asp Gly Gly Ser Ser Ser; SEQ ID NO:8) which contained a Bam HI cloning site (GGATCC=Gly Ser; SEQ ID NO:23) was introduced. The coding sequence was thus (nucleic acid sequence is SEQ ID NO:10, amino acid sequence is SEQ ID NO:22):

```
5'- GAA CTG AGT AGT GCC ACT GAC GGA GGA TCC TCA
TCG-3'
      camA  * Thr Asp Gly Gly Ser
                              *Bam HI*
```

The primer sequence shown below (SEQ ID NO:11) is the reverse complement used for PCR:

```
5'- CGA TGA GGA TCC TCC GTC AGT GGC ACT ACT CAG
TTC-3'
```

1.b Manipulations of the CamB Gene by PCR

For the camB gene the primer at the 5' end (SEQ ID NO:12) incorporated the second half of the peptide linker between the reductase and redoxin proteins, and the restriction site Bam HI for joining the two amplified genes together.

```
5'- TCA TCG GGA TCC TCA TCG ATG TCT AAA GTA GTG
TAT-3'
          Gly Ser Ser Ser ** camB
          *Bam HI*          Start
```

At the 3' end of camB the primer incorporates 12 nucleotides complementary to the end of camB followed by the stop codon TAA, a 6 nucleotide spacer before the GGAG ribosome binding site. Xba I and Hind III sites were then added to allow cloning of the camC gene when required. The sequence of the coding strand (SEQ ID NO:13) was therefore:

```
5'- CCC GAT AGG CAA TGG TAA TCA TCG GGAG TCT AGA GCA TCG AAG CTT TCA
TCG-3'
          CamB **stop   RBS Xba I    Hind III
```

The primer shown below is the reverse complement used for PCR (SEQ ID NO:14):

```
5'-CGA TGA AAG CTT CGA TGC TCT AGA CTCC CGA TGA TTA CCA TTG
CCT ATC GGG-3'.
```

1.c Preparation of the Full Fusion Construct

The camA and camB genes were amplified by the PCR using the primers described above. The new camA was digested with Eco RI and Bam HI, while the new CamB was digested with Bam HI and Hind III. The pGLW11 expression vector was digested with Eco RI and Hind III. All three were purified by agarose gel electrophoresis and the three gel slices containing the separate fragments were excised from the gel and ligated together, and then transformed into E. Coli DH5α. Successful ligation of all the fragments were confirmed by a series of restriction digestion experiments, especially the presence of the new and unique Xba I site. The entire sequence of the insert from the Eco RI site to the Hind III site was determined to ensure that all the sequences were correct.

The new plasmid, named pSGB$^{F1}$ was transformed into E. Coli and expression of the reductase and redoxin proteins was induced by IPTG. When a purified P450$_{cam}$ enzyme was added to the cell-free extract, substrate oxidation was observed for a variety of substrates.

When the camC gene is cloned into the pSGB$^F$ plasmid using the Xba I and Hind III restriction sites, the new recombinant plasmid thus generated expresses the reductase and redoxin as a fusion protein and the P450$_{cam}$ enzyme as a operate entity both from the same mRNA molecule. This in vivo system is catalytically competent for terpene oxidation in whole cells.

2. The In Vivo System with the Protein Expressed Separately

2.a The Basic Strategy

The starting point of the preparation of this in vivo system was the recombinant plasmid used to express the camA gene for putidaredoxin reductase. The camA gene was cloned into the pGLW11 plasmid using the Eco RI and Bam HI restriction sites, with Eco RI being at the 5' end of the gene. Conveniently the polylinker region of the pGLW11 vector has a Hind III site downstream of the Bam HI site. The camB gene was therefore manipulated by PCR such that it can be cloned into pGLW11 using the Bam HI and Hind III sites. This new plasmid expresses the reductase and redoxin as separate proteins.

The camB gene was cloned into pUC118 by the Bam HI and Hind III cloning sites to express putidaredoxin for our general in vitro substrate oxidation work. Therefore, the PCR primer at the 3' end of the camB gene was designed to introduce a ribosome binding site and the Xba I restriction site upstream of the Hind III site so that the camC gene can be inserted downstream of camB using the Xba I and Hind III sites. Therefore the three genes were cloned without fusion in the pGLW11 expression vector and arranged in the order 5'-camA-camB-camC-3', and each gene has its own RBS to initiate protein synthesis.

2.b Manipulations of the CamB Gene

We used the internal and unique restriction site Mlu I (recognition sequence ACGCGT) within the camB gene as the starting point so that the PCR product has a different size from the PCR template fragment. The primers were as follows:

```
5'- TCA TCG ACG CGT CGC GAA CTG CTG-3'
``` where the Mlu I site is in bold (SEQ ID NO:15).

The desired coding sequence at the 3' end of the camB gene was SEQ ID NO:16:

```
5'- CCC GAT AGG CAA TGG TAA GTA GGT GAA TAT CTA ATC CCC ATC
    camB      **stop
TAT GCG CGA GTG GAG TCT AGA GTT CGA-3'
         RBS      XbaI
```

After the stop codon there is a 35 base spacer before the RBS which is used to initiate the synthesis of the P450$_{cam}$ enzyme. The Xba I cloning site is located within the spacer between the RBS and the start codon (not in this primer) of the camC gene. The PCR primer used was the reverse complement of the sequence above. The PCR was carried out and the amplified fragment of the appropriate size was purified by agarose gel electrophoresis and the gel slice excised.

One extra step was necessary to complete the construction of the new plasmid. The plasmid for the fusion protein in vivo system was digested with Mlu I and Hind III restriction enzymes, purified by agarose gel electrophoresis, and the gel slice for the small camB fragment excised. The pUC118 plasmid for camB expression was similarly digested, and the gel slice for the backbone was excised. By ligating the two fragments together we prepared a new pUC118-based plasmid which had an Xba I site followed by an Hind III site downstream of the stop codon of camB. This new plasmid was digested with the Mlu I and Xba I enzymes and the backbone was ligated with the new camB fragment described above to generate a plasmid with the following arrangement of the key components:

. . . lac Promoter . . . Bam HI . . . camB gene . . . spacer . . . RBS . . . Xba I . . . Hind III . . .

2.c Preparation of the In Vivo System Plasmid

Once the modified camB with the Xba I and Hind III restriction sites and appropriate spacers were prepared, the in vivo system was constructed by cloning this into the pGLW11-based plasmid used to express the camA gene (reductase protein) using the Bam HI and Hind III sites. The new in vivo system vector has the following arrangement of the key components:

. . . tac Promoter . . . Eco IRI . . . RBS . . . camA gene . . . spacer . . . Bam HI . . . RBS . . . camB gene . . . spacer . . . RBS . . . Xba I . . . Hind III . . .

This new plasmid, named pSGB$^+$, was transformed into E. Coli and expression of the reductase and redoxin proteins was induced by IPTG. When a purified P450$_{cam}$ enzyme was added to the cell-free extract, substrate oxidation was observed for a variety of substrates.

When the camC gene is cloned into this pSGC$^+$ plasmid using the Xba I and Hind III restriction sites, the new recombinant plasmid thus generated will express the three proteins separately, each under the direction of its own RBS but from the same mRNA molecule. Thus constitutes the in vivo system used in the vast majority of our terpene oxidation work.

3. Introduction of an Xba I Site into pRH1091

This is the final step to enable the camC gene to be cloned into the in vivo systems by the two cloning sites XbaI and Hind III. The Xba I site was added by PCR of the entire pRH1091 plasmid using two primers. The presence of these two sites will also enable cloning of the camC gene into M13 since both Xba I and Hind III are unique in camC and M13.

The primers shown below maintain the Hind III cloning site AAGCTT:

```
5'-TCA TCG AAG CTT GGC TGT TTT-3'  (SEQ D NO:17)
       Hind III ** vector
```

At the other end the coding sequence desired was SEQ ID NO:18:

```
5'-ACA ATT TCA CAC AGGA TCT AGA C CAT ATG TCA TCG AAG CTT TCA TCG-3'
              Vector **RBS Xba I Nde I     Hind III
```

This sequence maintained the Nde I and Hind III sites but the new Xba I site was introduced upstream of the Nde I site. The PCR primer used was the reverse complement of the desired sequence (SEQ ID NO:19):

```
5'-CGA TGA AAG CTT CGA TGA CAT ATG GTC T AGA TCCT GTG TGA AAT TGT-3'.
```

The PCR product was then purified by agarose gel electrophoresis, digested with Hind III and circularised with T4 DNA ligase. Success of the PCR method was indicated by the presence of a new and unique Xba I site in plasmid DNA isolated from transformants.

4. Cloning of CamC into the In Vivo Systems

All existing camC mutants were cut out of pRH1091-based expression plastids with Nde I and Hind III. The new vector is similarly cut with the same restriction enzymes and the camC gene cloned into this plasmid with T4 DNA ligase.

This DNA is transformed into *E. Coli* JM109 which then may be grown to express P450$_{cam}$.

The camC gene is excised from the new vector using Xba I and Hind III restriction enzymes and cloned into either the in vivo vector systems or M13mp19 for mutagenesis.

5. In Vivo Expression and Substrate Turnover

For protein expression, cells are grown in LBamp medium (tryptone 10 g/liter, yeast extract 5 g/liter, NaCl 10 g/liter, 50 µg/ml ampicillin) at 30° C. until the OD$_{600\ nm}$ reaches 1.0–1.2. IPTG (isopropyl-β-D-thiogalactopyranoside) was added to a final concentration of 1 µM (from a 1 M stock in H$_2$O) and the culture was incubated at 30° C. overnight.

For simple screening the substrate can be added to culture and the incubation continued. However, due to impurities from the culture media the cells were generally washed twice with 0.5 vol. of buffer P, (KH$_2$PO$_4$ 6.4 g, K$_2$HPO$_4$.3H$_2$O 25.8 g, H$_2$O to 4 liters, pH 7.4) and resuspended in 0.25 vol. oxygen saturated buffer P containing 24 mM glucose. Substrate was added to 1 mM and the incubation continued at 30° C. The reaction was allowed to run for 24 hours with periodic additions of substrate and glucose.

The reaction was analysed by extracting 1 ml of the incubation mixture with 250 µl of ethylacetate. After centrifuging in a microcentrifuge at 13,000 g for 2 minutes, 2 µl of the organic extract was injected onto a 0.25 mm×30 m DB-1 gas chromatography column in a Fisons GC 8000 series gas chromatograph. The samples were carried through the column using helium carrier gas and the compounds present were detected using a flame ionisation detector.

A variety of temperature programmes were used for different substrate to resolve turnover products.

| Monoterpenes | |
| --- | --- |
| Injector temperature | 150° C. |
| Detector temperature | 250° C. |
| Oven temperature | 120° C. for 15 min–200° C. at 25° C./min, 200° C. for 1 min. |
| Sesquiterpenes | |
| Injector temperature | 250° C. |
| Detector temperature | 250° C. |
| Oven temperature | 150° C.–230° C. at 5° C./min, 230° C. for 1 min. |

Results for particular oxidation reactions are shown in table 6 and in the Figures.

FIG. 1 shows the result of an oxidation reaction with camphor. The 5-ketocamphor arises from further oxidation of 5-exo-hydroxycamphor. As can be seen there is surprisingly little of the further oxidation occurring in the presence of camphor.

EXAMPLE 4

A Second In Vivo Expression System

The cluster of genes for the expression of the three proteins of the P450$_{cam}$ system, as described in Example 3, were also expressed in whole *E. coli* cells using the pCW vector. This vector utilises two tac promoters arranged in line to increase protein expression. It has a RBS, and contains the gene conferring resistance to the antibiotic ampicillin (Barnes, H. J. *Methods Enzymol.* 1996, 272, 3–14).

Both methods of expressing catalytically competent P450$_{cam}$ systems described in Example 3 were successful with the pCW vector. Thus the fusion system, where putidaredoxin reductase and putidaredoxin were expressed as a fusion protein with an oligopeptide linker, but the P450$_{cam}$ monooxygenase was expressed but not fused to the electron transfer proteins. The second system expressed all three proteins as separate entities in the same *E. coli* host.

1. The Fusion Protein System

A new plasmid was constructed by cloning the gene for the fusion of electron transfer proteins into pCW so that different P450$_{cam}$ mutants could be introduced into the system by cloning. The 5' end oligonucleotide used for the PCR amplification of the cam A gene introduced not only the Eco RI site for cloning into the pGL W11 vector but also a Nde I site which spans the ATG start codon of the gene (see Example 3, section 1a). In the pCW vector there is a Nde I site positioned downstream of the RBS for cloning of the gene to be expressed. The pGL W11 vector containing the camA-camB fusion gene was digested with Nde I and Hind III, and the insert purified by agarose gel electrophoresis. The pCW vector system was also digested with these two enzymes and the linearised vector purified by the same method. The two fragments were ligated with DNA ligase to generate the new pCWSGB$_F$ plasmid based on the pCW vector and which expressed the fusion of the electron transfer proteins. The insert excised from the pGL W11-based plasmid already contained a RBS for protein expression and an Xba I site just upstream of the Hind III site (see Example 3, section 2.c), so that the cam C gene encoding P450$_{cam}$ mutants can be cloned using these two sites and expressed off the RBS. Therefore genes encoding the P450$_{cam}$ mutants can be excised from the modified pRH system and cloned into the new pCWSGB$_F$ plasmid using the Xba I and Hind III sites.

2. The Three Proteins Expressed Separately

This system was generated in exactly the same way as for the fusion system. Thus the pSGB+ plasmid was digested with the Nde I and Hind III restriction enzymes and the insert cloned into the pCW vector. This new plasmid pCWSGB+ expressed putidaredoxin reductase and putidaredoxin as separate entities off the twin tac promoters of the pCW vector. The P450$_{cam}$ mutants were introduced into this vector using the Xba I and Hind III sites.

3. In Vivo Expression and Substrate Turnover

The conditions described below were used for test purposes in shake flasks in a laboratory and were not optimised. Under proper fermenter conditions with higher expression and biomass the final yield of products will be much increased.

*E. coli* DH5α cells harbouring either of the catalytically competent P450$_{cam}$ systems were grown from a single colony on an agar plate in 1 L of LBamp medium at 30° C. until OD$_{600\ nm}$ reached ca. 1. IPTG was added to 1 mM final concentration (from a 1 M stock in water) and the culture grown for a further 6 h. The final OD$_{600\ nm}$ were in the range 2.0–2.5. Cells were harvested by centrifugation at 5000 g and washed once with 40 mM phosphate buffer, pH 7.4. The cell pellet was resuspended in 500 ml of 40 mM phosphate buffer, pH 7.4. Glucose was added as a 2 M stock to a final concentration of 100 mM, and 1 mL of the substrate (α-pinene or R-limonene) was added to start the reaction. The mixture was shaken in an open 2 L conical flask in an orbital incubator at 200 rpm. More glucose was added every 24 h (100 mM final concentration based on a 500 mL volume, from a 2 M stock) and more substrate (1 mL) was added every 12 h. The progress of the reaction was monitored by GC and the whole cell system was active for at least 5 days at ambient temperatures and the minimum yield at the end of day 5, as assayed by extraction of the reaction medium with chloroform and analysing by GC, was 100 mg of products without accounting for volatilisation of products into the atmosphere and condensation on the flask above the liquid level. In addition, no compounds arising from further hydroxylation at another carbon atom were observed when the substrate was present.

EXAMPLE 5

In Vitro and In Vivo Substrate Oxidation by P450$_{BM-3}$

In a typical reaction in vitro (optional 30° C. temperature control) the 1.5 mL incubation mixture contained 40 mM phosphate buffer, pH 8.0, 1 µM P450$_{BM-3}$, 50 µg/mL of catalase, and terpene substrates were added as a 1 M stock in ethanol to a final concentration of 2 mM. NADPH was added typically to 400 µM final concentration, and the rates of reaction could be monitored at 340 nm. After all the NADPH had been consumed, the mixture was extracted by vortexing with 0.5 mL of chloroform, the phases separated by centrifugation, and the organic phase could be analysed by GC using the programs described in Example 3.

Catalase does not catalyse the substrate oxidation reaction but rather it is present to remove any hydrogen by-product which could otherwise denature the enzyme. The method can be increased in scale to, for example, 20 mL total incubation volume to allow purification of sufficient produces by HPLC for spectroscopic characterisation. Fresh substrate (1 mM) and NADPH (1–2 mM) are added periodically, such as every 20 minutes in a total reaction time of, typically 3 hours.

Since the P450$_{BM-3}$ enzyme is catalytically self-sufficient, i.e., both the monooxygenase and electron transfer domains are in a single polypeptide, the enzyme as expressed in *E. coli* can be used for whole cell, in vivo substrate oxidations. The procedure described under Example 3 for in vivo substrate oxidation by the P450$_{cam}$ enzyme can also be used for the P450$_{BM-3}$ enzyme.

TABLE 1

Limonene

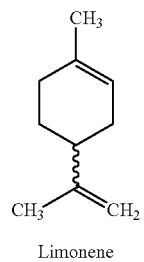

α-pinene

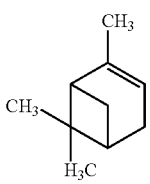

TABLE 1-continued

β-pinene

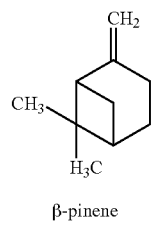

α-terpinene

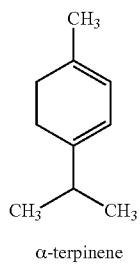

γ-terpinene

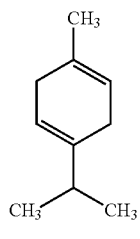

(+)-sabinene

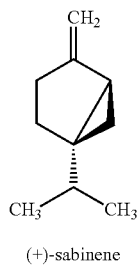

(−)-α-thujene

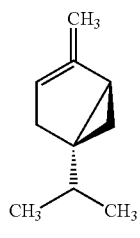

myrcene

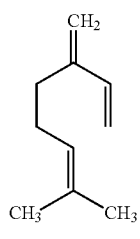

TABLE 1-continued
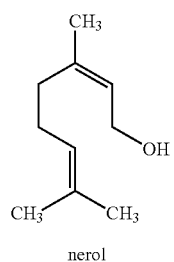
nerol
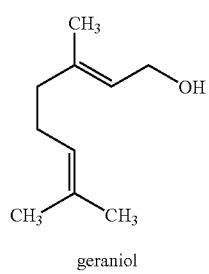
geraniol
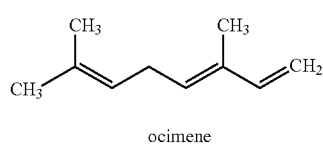
ocimene
TABLE 2
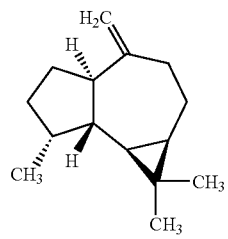
(+)-Aromadendrene
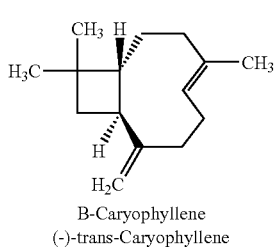
B-Caryophyllene
(-)-trans-Caryophyllene
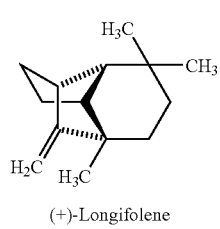
(+)-Longifolene
TABLE 2-continued
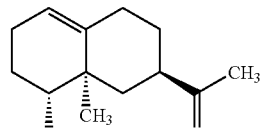
(+)-Valencene
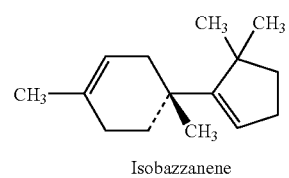
Isobazzanene
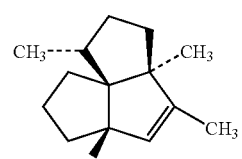
Silphinene
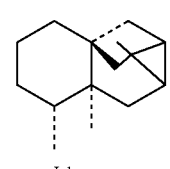
Ishwarane
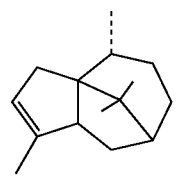
Isopatchchoul-3-ene
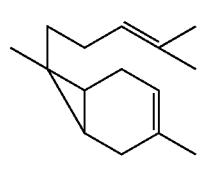
Isosesquicarene
TABLE 3
HYDROPATHY SCALE FOR AMINO ACID SIDE CHAINS
| Side Chain | Hydropathy |
|---|---|
| Ile | 4.5 |
| Val | 4.2 |
| Leu | 3.8 |
| Phe | 2.8 |
| Cys | 2.5 |
| Met | 1.9 |
| Ala | 1.8 |
| Gly | −0.4 |
| Thr | −0.7 |
| Ser | −0.8 |

TABLE 3-continued

HYDROPATHY SCALE FOR AMINO ACID SIDE CHAINS

| Side Chain | Hydropathy |
|---|---|
| Trp | −0.9 |
| Tyr | −1.3 |
| Pro | −1.6 |
| His | −3.2 |
| Glu | −3.5 |
| Gln | −3.5 |
| Asp | −3.5 |
| Asn | −3.5 |
| Lys | −3.9 |
| Arg | −4.5 |

TABLE 4

P450$_{cam}$ mutants
All mutants optionally contain the base mutation C334A.

Single mutants: Y96A, Y96F, Y96L, Y96W.

Double mutants:

| | | | | |
|---|---|---|---|---|
| Y96A-F87A | Y96F-F87A | Y96F-V295A | Y96L-F87A | Y96L-A296L |
| Y96A-F87L | Y96F-F87I | Y96F-V295L | Y96L-F87L | Y96L-A296F |
| Y96A-F87W | Y96F-F87L | Y96F-V295I | Y96L-F98W | Y96L-V396A |
| Y96A-F98W | Y96F-F87W | Y96F-A296L | Y96L-T101L | Y96L-V396L |
| Y96A-L244A | Y96F-F98W | Y96F-A296F | Y96L-T101F | Y96L-V396F |
| Y96A-V247A | Y96F-T101L | Y96F-I395F | Y96L-L244A | Y96L-V396W |
| Y96A-V247L | Y96F-T101F | Y96F-I395G | Y96L-L244F | Y96W-F87W |
| Y96A-I395F | Y96F-T185A | Y96F-V396A | Y96L-V247A | Y96W-F98W |
| Y96A-I395G | Y96F-T185F | Y96F-V396L | Y96L-V247L | Y96W-L244A |
| | Y96F-T185L | Y96F-V396F | Y96L-V247F | Y96W-V247A |
| | Y96F-L244A | Y96F-V396W | Y96L-V247W | Y96W-V396A |
| | Y96F-V247A | | Y96L-G248L | |
| | Y96F-V247L | | Y96L-V295L | |
| | Y96F-G248L | | Y96L-V295F | |

Triple Mutants:

| | | |
|---|---|---|
| Y96A-F87A-L244A | Y96L-V247A-V396L | Y96F-F87W-V247A |
| Y96A-F87A-V247A | Y96L-V247A-V396F | Y96F-F87W-V247L |
| Y96A-F87L-L244A | Y96L-V247A-V396W | Y96F-F87W-V247F |
| Y96A-F87L-V247A | Y96L-V247F-V396A | Y96F-F87W-V295L |
| Y96A-L244A-V247A | Y96F-F87A-L244A | Y96F-F87W-A296L |
| Y96L-F87A-L244A | Y96F-F87A-V247A | Y96F-F87W-V396A |
| Y96L-F87A-V247A | Y96F-F87A-V247L | Y96F-F87W-V396L |
| Y96L-F87L-L244A | Y96F-F87A-I395F | Y96F-V247F-V396A |
| Y96L-F87L-V247A | Y96F-F87A-I395G | Y96F-L244A-V396L |
| Y96L-V247A-I395F | Y96F-F87L-V247A | Y96F-L244A-V396F |
| Y96L-V247L-I395F | Y96F-F87L-V247L | Y96F-L244A-V396W |
| Y96L-V247L-I395G | Y96F-F87L-I395F | Y96F-L244F-V396A |
| Y96L-L244A-V396L | Y96F-F87W-T185A | Y96F-V247A-V396L |
| Y96L-L244A-V396F | Y96F-F87W-T185F | Y96F-V247A-V396F |
| Y96L-L244A-V396W | Y96F-F87W-T185L | Y96F-V247A-V396W |
| Y96L-L244F-V396A | Y96F-F87W-L244F | Y96W-F87W-F98W |

| Four mutations: | Five mutations: |
|---|---|
| Y96A-F87A-L244A-V247A | Y96F-F87W-T185L-V247L-V295L |
| Y96A-F87L-L244A-V247A | Y96F-F87W-T185L-V247L-V396A |
| Y96L-F87A-L244A-V247A | Y96F-F87W-T185L-V247L-V396L |
| Y96L-F87L-L244A-V247A | |
| Y96F-F87W-L244A-V295L | |
| Y96F-F87W-L244F-V396A | |
| Y96F-F87W-L244A-A296L | |
| Y96F-F87W-V247A-V396L | |

TABLE 4-continued

P450$_{cam}$ mutants
All mutants optionally contain the base mutation C334A.

Y96F-F87W-V247A-V396F
Y96F-F87W-V247L-V295A
Y96F-F87W-V247L-V396A
Y96F-F87W-V247F-V396A
Y96F-F87W-V247A-I395F
Y96F-F87W-V247L-I395G

TABLE 5

P450$_{BM-3}$ mutants

| | | | | |
|---|---|---|---|---|
| R47L-Y51F | R47L-Y51F-F42A | R47L-Y51F-F87A | R47L-Y51F-A264V | R47L-Y51F-I263F-A264L |
| R47A-Y51A | R47L-Y51F-F42L | R47L-Y51F-F87W | R47L-Y51F-A264L | R47L-Y51F-I263W-A264I |
| R47A-Y51L | R47A-Y51L-F42L | R47L-Y51F-I263A | R47L-Y51F-A264I | |
| | | R47L-Y51F-I263F | R47L-Y51F-M354L | |
| | | R47L-Y51F-I263L | R47L-Y51F-M354A | |
| | | R47L-Y51F-I263W | | |
| | R47L-Y51F-L75A-M354L | | R47L-Y51F-L181A | |
| | R47A-Y51L-L75A-M354A | | R47L-Y51F-L181W | |
| | R47L-Y51F-F87W-A264L | | | |
| | R47L-Y51F-F87W-A264I | | | |
| | R47L-Y51F-F87W-A264F | | | |

TABLE 6

Summary of changes in selectivity of terpene oxidation by P450$_{cam}$ mutants. Approximate proportions of only the products arising from the insertion of a single oxygen atom, i.e., alcohols and epoxides, are given.

| Mutant | Products, some also indicated by their retention times (min) on a 30 m DB-1 fused silica GC column | | | | | Comments |
|---|---|---|---|---|---|---|
| L-Limonene | 5.23–5.33 min 1,2-Oxide | 6.10–6.20 min Product | 6.60–6.70 min Isopiperitenol | 7.05–7.15 min Carveol | 8.15–8.25 min Product | |
| Wild-type | — | 30% | 70% | — | — | Very small quantities |
| F87I-Y96F | 8% | 5% | 5% | 2% | 80% | |
| Y96F-V247L | 5% | — | >85% | 5% | <5% | Other small peaks observed |
| Y96F-T185L | 5% | <2% | >90% | <2% | <2% | Other small peaks observed |
| F87W-Y96F-V247L | <2% | — | >95% | <2% | — | |
| F87L-Y96F-V247L | 5% | 5% | 5% | 2% | >80% | |

| α-Pinene | Pinene oxide | Verbenol | Verbenone | | | |
|---|---|---|---|---|---|---|
| Wild-type | 10% | 30% | 10% | | | Remaining 50% other products |
| Y96F-V247A | 10% | 50% | 20% | | | Remaining 20% other products |
| Y96F | 10% | 30% | 15% | | | Many other products |
| F87W-Y96F-V247L | — | 70% | 15% | | | Very few other products |

| Valencene | Nookatol region | | Nookatone | Product | Product | |
|---|---|---|---|---|---|---|
| | 9.60–9.70 min | 9.80–9.90 min | 11.3–11.4 min | 13.0–13.1 min | 14.0–14.1 min | |
| Wild-type | — | — | — | — | — | Many small peaks |
| Y96F-V247A | 30% | 15% | 10% | <10% | >30% | |
| Y96L-V247A | 15% | 20% | 10% | >40% | 10% | |

| γ-Terpinene | 5.70–5.80 min | 6.20–6.30 min | | | | |
|---|---|---|---|---|---|---|
| Y96F | 15% | 85% | | | | |

TABLE 7

P450cam wild-type sequence

```
acg act gaa acc ata caa agc aac gcc aat ctt gcc cct ctg cca ccc    48
Thr Thr Glu Thr Ile Gln Ser Asn Ala Asn Leu Ala Pro Leu Pro Pro
1               5                   10                  15 cat gtg cca gag cac ctg gta ttc gac ttc gac atg tac aat ccg tcg    96
His Val Pro Glu His Leu Val Phe Asp Phe Asp Met Tyr Asn Pro Ser
                20                  25                  30
```

TABLE 7-continued

P450cam wild-type sequence

| | | | | | | | | | | | | | | | | |
|---|---|---|---|---|---|---|---|---|---|---|---|---|---|---|---|---|
| aat | ctg | tct | gcc | ggc | gtg | cag | gag | gcc | tgg | gca | gtt | ctg | caa | gaa | tca | 144 |
| Asn | Leu | Ser | Ala | Gly | Val | Gln | Glu | Ala | Trp | Ala | Val | Leu | Gln | Glu | Ser | |
| | | 35 | | | | 40 | | | | | 45 | | | | | |
| aac | gta | ccg | gat | ctg | gtg | tgg | act | cgc | tgc | aac | ggc | gga | cac | tgg | atc | 192 |
| Asn | Val | Pro | Asp | Leu | Val | Trp | Thr | Arg | Cys | Asn | Gly | Gly | His | Trp | Ile | |
| | 50 | | | | 55 | | | | | 60 | | | | | | |
| gcc | act | cgc | ggc | caa | ctg | atc | cgt | gag | gcc | tat | gaa | gat | tac | cgc | cac | 240 |
| Ala | Thr | Arg | Gly | Gln | Leu | Ile | Arg | Glu | Ala | Tyr | Glu | Asp | Tyr | Arg | His | |
| 65 | | | | 70 | | | | | 75 | | | | | 80 | | |
| ttt | tcc | agc | gag | tgc | ccg | ttc | atc | cct | cgt | gaa | gcc | ggc | gaa | gcc | tac | 288 |
| Phe | Ser | Ser | Glu | Cys | Pro | Phe | Ile | Pro | Arg | Glu | Ala | Gly | Glu | Ala | Tyr | |
| | | | | 85 | | | | | 90 | | | | | 95 | | |
| gac | ttc | att | ccc | acc | tcg | atg | gat | ccg | ccc | gag | cag | cgc | cag | ttt | cgt | 336 |
| Asp | Phe | Ile | Pro | Thr | Ser | Met | Asp | Pro | Pro | Glu | Gln | Arg | Gln | Phe | Arg | |
| | | | 100 | | | | | 105 | | | | | 110 | | | |
| gcg | ctg | gcc | aac | caa | gtg | gtt | ggc | atg | ccg | gtg | gtg | gat | aag | ctg | gag | 384 |
| Ala | Leu | Ala | Asn | Gln | Val | Val | Gly | Met | Pro | Val | Val | Asp | Lys | Leu | Glu | |
| | | 115 | | | | | 120 | | | | | 125 | | | | |
| aac | cgg | atc | cag | gag | ctg | gcc | tgc | tcg | ctg | atc | gag | agc | ctg | cgc | ccg | 432 |
| Asn | Arg | Ile | Gln | Glu | Leu | Ala | Cys | Ser | Leu | Ile | Glu | Ser | Leu | Arg | Pro | |
| | 130 | | | | | 135 | | | | | 140 | | | | | |
| caa | gga | cag | tgc | aac | ttc | acc | gag | gac | tac | gcc | gaa | ccc | ttc | ccg | ata | 480 |
| Gln | Gly | Gln | Cys | Asn | Phe | Thr | Glu | Asp | Tyr | Ala | Glu | Pro | Phe | Pro | Ile | |
| 145 | | | | | 150 | | | | | 155 | | | | | 160 | |
| cgc | atc | ttc | atg | ctg | ctc | gca | ggt | cta | ccg | gaa | gaa | gat | atc | ccg | cac | 528 |
| Arg | Ile | Phe | Met | Leu | Leu | Ala | Gly | Leu | Pro | Glu | Glu | Asp | Ile | Pro | His | |
| | | | | 165 | | | | | 170 | | | | | 175 | | |
| ttg | aaa | tac | cta | acg | gat | cag | atg | acc | cgt | ccg | gat | ggc | agc | atg | acc | 576 |
| Leu | Lys | Tyr | Leu | Thr | Asp | Gln | Met | Thr | Arg | Pro | Asp | Gly | Ser | Met | Thr | |
| | | | 180 | | | | | 185 | | | | | 190 | | | |
| ttc | gca | gag | gcc | aag | gag | gcg | ctc | tac | gac | tat | ctg | ata | ccg | atc | atc | 624 |
| Phe | Ala | Glu | Ala | Lys | Glu | Ala | Leu | Tyr | Asp | Tyr | Leu | Ile | Pro | Ile | Ile | |
| | | | | 195 | | | | | 200 | | | | | 205 | | |
| gag | caa | cgc | agg | cag | aag | ccg | gga | acc | gac | gct | atc | agc | atc | gtt | gcc | 672 |
| Glu | Gln | Arg | Arg | Gln | Lys | Pro | Gly | Thr | Asp | Ala | Ile | Ser | Ile | Val | Ala | |
| | 210 | | | | | 215 | | | | | 220 | | | | | |
| aac | ggc | cag | gtc | aat | ggg | cga | ccg | atc | acc | agt | gac | gaa | gcc | aag | agg | 720 |
| Asn | Gly | Gln | Val | Asn | Gly | Arg | Pro | Ile | Thr | Ser | Asp | Glu | Ala | Lys | Arg | |
| 225 | | | | | 230 | | | | | 235 | | | | | 240 | |
| atg | tgt | ggc | ctg | tta | ctg | gtc | ggc | ggc | ctg | gat | acg | gtg | gtc | aat | ttc | 768 |
| Met | Cys | Gly | Leu | Leu | Leu | Val | Gly | Gly | Leu | Asp | Thr | Val | Val | Asn | Phe | |
| | | | | 245 | | | | | 250 | | | | | 255 | | |
| ctc | agc | ttc | agc | atg | gag | ttc | ctg | gcc | aaa | agc | ccg | gag | cat | cgc | cag | 816 |
| Leu | Ser | Phe | Ser | Met | Glu | Phe | Leu | Ala | Lys | Ser | Pro | Glu | His | Arg | Gln | |
| | | | 260 | | | | | 265 | | | | | 270 | | | |
| gag | ctg | atc | gag | cgt | ccc | gag | cgt | att | cca | gcc | gct | tgc | gag | gaa | cta | 864 |
| Glu | Leu | Ile | Glu | Arg | Pro | Glu | Arg | Ile | Pro | Ala | Ala | Cys | Glu | Glu | Leu | |
| | | | 275 | | | | | 280 | | | | | 285 | | | |
| ctc | cgg | cgc | ttc | tcg | ctg | gtt | gcc | gat | ggc | cgc | atc | ctc | acc | tcc | gat | 912 |
| Leu | Arg | Arg | Phe | Ser | Leu | Val | Ala | Asp | Gly | Arg | Ile | Leu | Thr | Ser | Asp | |
| | | | 290 | | | | | 295 | | | | | 300 | | | |
| tac | gag | ttt | cat | ggc | gtg | caa | ctg | aag | aaa | ggt | gac | cag | atc | ctg | cta | 960 |
| Tyr | Glu | Phe | His | Gly | Val | Gln | Leu | Lys | Lys | Gly | Asp | Gln | Ile | Leu | Leu | |
| 305 | | | | | 310 | | | | | 315 | | | | | 320 | |
| ccg | cag | atg | ctg | tct | ggc | ctg | gat | gag | cgc | gaa | aac | gcc | tgc | ccg | atg | 1008 |
| Pro | Gln | Met | Leu | Ser | Gly | Leu | Asp | Glu | Arg | Glu | Asn | Ala | Cys | Pro | Met | |
| | | | | 325 | | | | | 330 | | | | | 335 | | |

TABLE 7-continued

P450cam wild-type sequence

| | | | | | | | | | | | |
|---|---|---|---|---|---|---|---|---|---|---|---|
| cac | gtc | gac | ttc | agt | cgc | caa | aag | gtt | tca | cac | acc | acc | ttt | ggc | cac | 1056 |
| His | Val | Asp | Phe | Ser | Arg | Glu | Lys | Val | Ser | His | Thr | Thr | Phe | Gly | His |
| | | | 340 | | | | 345 | | | | | 350 | | | |

```
ggc agc cat ctg tgc ctt ggc cag cac ctg gcc cgc cgg gaa atc atc    1104
Gly Ser His Leu Cys Leu Gly Gln His Leu Ala Arg Arg Glu Ile Ile
            355                 360                 365 gtc acc ctc aag gaa tgg ctg acc agg att cct gac ttc tcc att gcc    1152
Val Thr Leu Lys Glu Trp Leu Thr Arg Ile Pro Asp Phe Ser Ile Ala
        370                 375                 380 ccg ggt gcc cag att cag cac aag agc ggc atc gtc agc ggc gtg cag    1200
Pro Gly Ala Gln Ile Gln His Lys Ser Gly Ile Val Ser Gly Val Gln
385                 390                 395                 400 gca ctc cct ctg gtc tgg gat ccg gcg act acc aaa gcg gta            1242
Ala Leu Pro Leu Val Trp Asp Pro Ala Thr Thr Lys Ala Val
                405                 410                 414
```

TABLE 8

P450$_{BM-3}$ sequence

```
1   /     1                           31    /    11
atg aca att aaa gaa atg cct cag cca aaa acg ttt gga gag ctt aaa aat tta ccg tta
Met Thr Ile Lys Glu Met Pro Gln Pro Lys Thr Phe Gly Glu Leu Lys Asn Leu Pro Leu 61  /    21                           91    /    31
tta aac aca gat aaa ccg gtt caa gct ttg atg aaa att gcg gat gaa tta gga gaa atc
Leu Asn Thr Asp Lys Pro Val Gln Ala Leu Met Lye Ile Ala Asp Glu Leu Gly Glu Ile 121 /    41                           151   /    51
ttt aaa ttc gag gcg cct ggt cgt gta acg cgc tac tta tca gtc agc gta cta att aaa
Phe Lys Phe Glu Ala Pro Gly Arg Val Thr Arg Tyr Leu Ser Ser Gln Arg Leu Ile Lys 181 /    61                           211   /    71
gaa gca tgc gat gaa tca cgc ttt gat aaa aac tta agt caa gcg ctt aaa ttt gta cgt
Glu Ala Cys Asp Glu Ser Arg Phe Asp Lys Asn Leu Ser Gln Ala Leu Lys Phe Val Arg 241 /    81                           271   /    91
gat ttt gca gga gac ggg tta ttt aca agc tgg acg cat gaa aaa aat tgg aaa aaa gcg
Asp Phe Ala Gly Asp Gly Leu Phe Thr Ser Trp Thr His Glu Lys Asn Trp Lys Lys Ala 301 /    101                          331   /    111
cat aat atc tta ctt cca agc ttc agt cag cag gca atg aaa ggc tat cat gcg atg atg
His Asn Ile Leu Leu Pro Ser Phe Ser Gln Gln Ala Met Lys Gly Tyr His Ala Met Met 361 /    121                          391   /    131
gtc gat atc gcc gtg cag ctt gtt caa aag tgg gag cgt cta aat gca gat gag cat att
Val Asp Ile Ala Val Gln Leu Val Gln Lys Trp Glu Arg Leu Asn Ala Asp Glu His Ile 421 /    141                          451   /    151
gaa gta ccg gaa gac atg aca cgt tta acg ctt gat aca att ggt ctt tgc ggc ttt aac
Glu Val Pro Glu Asp Met Thr Arg Leu Thr Leu Asp Thr Ile Gly Leu Cys Gly Phe Asn 481 /    161                          511   /    171
tat cgc ttt aac agc ttt tac cga gat cag cct cat cca ttt att aca agt atg gtc cgt
Tyr Arg Phe Asn Ser Phe Tyr Arg Asp Gln Pro His Pro Phe Ile Thr Ser Met Val Arg 541 /    181                          571   /    191
gca ctg gat gaa gca atg aaa aag ctg cag cga gca aat cca gac gac cca gct tat gat
Ala Leu Asp Glu Ala Met Asn Lys Leu Gln Arg Ala Asn Pro Asp Asp Pro Ala Tyr Asp 601 /    201                          631   /    211
gaa aac aag cgc cag ttt caa gaa gat atc aag gtg atg aac gac cta gta gat aaa att
Glu Asn Lys Arg Gln Phe Gln Glu Asp Ile Lys Val Met Asn Asp Leu Val Asp Lys Ile 661 /    221                          691   /    231
att gca gat cgc aaa gca agc ggt gaa caa agc gat gat tta tta acg cat atg cta aac
Ile Ala Asp Arg Lys Ala Ser Gly Glu Gln Ser Asp Asp Leu leu Thr His Met Leu Asn 721 /    241                          751   /    251
gga aaa gat cca gaa acg ggt gag ccg ctt gat gac gag aaa att cgc tat caa att att
```

TABLE 8-continued

P450$_{BM-3}$ sequence

```
                    Gly Lys Asp Pro Glu Thr Gly Glu Pro Leu Asp Asp Glu Asn Ile Arg Tyr Gln Ile Ile

781  /      261                                 811  /      271
aca ttc tta att gcg gga cac gaa aca aca agt ggt ctt tta tca ttt gcg ctg tat ttc
Thr Phe Leu Ile Ala Gly His Glu Thr Thr Ser Gly Leu Leu Ser Phe Ala leu Tyr Phe 841  /      281                                 871  /      291
tta gtg aaa aat cca cat gta tta caa aaa gca gca gaa gaa gca gca cga gtt cta gta
Leu Val Lys Asn Pro His Val Leu Gln Lys Ala Ala Glu Glu Ala Ala Arg Val Leu Val 901  /      301                                 931  /      311
gat cct gct cca agc tac aaa caa gtc aaa cag ctt aaa tat gtc ggc atg gtc tta aac
Asp Pro Val Pro Ser Tyr Lys Gln Val Lys Gln Leu Lys Tyr Val Gly Met Val Leu Asn 961  /      321                                 991  /      331
gaa gcg ctg cgc tta tgg cca act gct cct gcg ttt tcc cta tat gca aaa gaa gat acg
Gln Ala Leu Arg Leu Trp Pro Thr Ala Pro Ala Phe Ser Leu Tyr Ala Lye Glu Asp Thr 1021 /      341                                 1051 /      351
gtg ctt gga gga gaa tat cct tta gaa aaa ggc gac gaa cta atg gtt ctg att cct cag
Val Leu Gly Gly Gln Tyr Pro Leu Gln Lys Gly Asp Gln Leu Met Val Leu Ile Pro Gln 1081 /      361                                 1111 /      371
ctt cac cgt gat aaa aca att tgg gga gac gat gtg gaa gag ttc cgt cca gag cgt ttt
Leu His Arg Asp Lys Thr Ile Trp Gly Asp Asp Val Gln Glu Phe Arg Pro Glu Arg Phe 1141 /      381                                 1171 /      391
gaa aat cca agt gcg att ccg cag cat gcg ttt aaa ccg ttt gga aac ggt cag cgt gcg
Glu Asn Pro Ser Ala Ile Pro Gln His Ala Phe Lys Pro Phe Gly Asn Gly Gln Arg Ala 1201 /      401                                 1231 /      411
tgt atc ggt cag cag ttc gct ctt cat gaa gca acg ctg gta ctt ggt atg atg cta aaa
Cys Ile Gly Gln Gln Phe Ala Leu His Glu Ala Thr Leu Val Leu Gly Met Met Leu Lys 1261 /      421                                 1291 /      431
cac ttt gac ttt gaa gat cat aca aac tac gag ctg gat att aaa gaa act tta acg tta
His Phe Asp Phe Glu Asp His Thr Asn Tyr Glu Leu Asp Ile Lys Glu Thr Leu Thr Leu 1321 /      441                                 1351 /      451
aaa cct gaa ggc ttt gtg gta aaa gca aaa tcg aaa aaa att ccg ctt ggc ggt att cct
Lys Pro Glu Gly Phe Val Val Lys Ala Lys Ser Lys Lys Ile Pro Leu Gly Gly Ile Pro 1381 /      461                                 1411 /      471
tca cct agc act gaa cag tct gcc aaa aaa gca cgc aaa aag gca gaa aac gct cat aat
Ser Pro Ser Thr Glu Gln Ser Ala Lys Lys Val Arg Lys Lye Ala Glu Asn Ala His Asn 1441 /      481                                 1471 /      491
acg ccg ctg ctt gtg cta tac ggt tca aat atg gga aca gct gaa gga acg gcg cgt gat
Thr Pro Leu Leu Val Leu Tyr Gly Ser Asn Met Gly Thr Ala Glu Gly Thr Ala Arg Asp 1501 /      501                                 1531 /      511
tta gca gat att gca atg agc aaa gga ttt gca ccg cag gtc gca acg ctt gat tca cac
Leu Ala Asp Ile Ala Met Ser Lys Gly Phe Ala Pro Gln Val Ala Thr Leu Asp Ser His 1561 /      521                                 1591 /      531
gcc gga aat ctt ccg cgc gaa gga gct gta tta att gta acg gcg tct tat aac ggt cat
Ala Gly Asn Leu Pro Arg Glu Gly Ala Val Leu Ile Val Thr Ala Ser Tyr Asn Gly His 1621 /      541                                 1651 /      551
ccg cct gat aac gca aag caa ttt gtc gac tgg tta gac caa gcg tct gct gat gaa gta
Pro Pro Asp Asn Ala Lys Gln Phe Val Asp Trp Leu Asp Gln Ala Ser Ala Asp Glu Val 1681 /      561                                 1711 /      571
aaa ggc gtt cgc tac tcc gta ttt gga tgc ggc gat aaa aac tgg gct act acg tat caa
Lye Gly Val Arg Tyr Ser Val Phe Gly Cys Gly Asp Lys Asn Trp Ala Thr Thr Tyr Gln 1741 /      581                                 1771 /      591
aaa gtg cct gct ttt atc gat gaa acg ctt gcc gct aaa ggg gca gaa aac atc gct gac
Lys Val Pro Ala Phe Ile Asp Glu Thr Leu Ala Ala Lys Gly Ala Glu Asn Ile Ala Asp 1801 /      601                                 1831 /      611
cgc ggt gaa gca gat gca agc gac gac ttt gaa ggc aca tat gaa gaa tgg cgt gaa cat
Arg Gly Glu Ala Asp Ala Ser Asp Asp Phe Glu Gly Thr Tyr Glu Glu Trp Arg Glu His 1861 /      621                                 1891 /      631
atg tgg agt gac gta gca gcc tac ttt aac ctc gac att gaa aac agt gaa gat aat aaa
Met Trp Ser Asp Val Ala Ala Tyr Phe Asn Leu Asp Ile Glu Asn Ser Glu Asp Asn Lys
```

TABLE 8-continued

P450<sub>BM-3</sub> sequence

```
1921 /     641                        1951 /     651
tct act ctt tca ctt caa ttt gtc gac agc gcc gcg gat atg ccg ctt gcg aaa atg cac
Ser Thr Leu Ser Leu Gln Phe Val Asp Ser Ala Ala Asp Met Pro Leu Ala Lys Met His 1981 /     661                        2011 /     671
ggt gcg ttt tca acg aac gtc gta gca agc aaa gaa ctt caa cag cca ggc agt gca cga
Gly Ala Phe Ser Thr Asn Val Val Ala Ser Lys Glu Leu Gln Gln Pro Gly Ser Ala Arg 2041 /     681                        2071 /     691
agc acg cga cat ctt gaa att gaa ctt cca aaa gaa gct tct tat caa gaa gga gat cat
Ser Thr Arg His Leu Glu Ile Glu Leu Pro Lys Glu Ala Ser Tyr Gln Glu Gly Asp His 2101 /     701                        2131 /     711
tta ggt gtt att cct cgc aac tat gaa gga ata gta aac cgt gta aca gca agg ttc ggc
Leu Gly Val Ile Pro Arg Asn Tyr Glu Gly Ile Val Asn Arg Val Thr Ala Arg Phe Gly 2161 /     721                        2191 /     731
cta gat gca tca cag caa atc cgt ctg gaa gca gaa gaa gaa aaa tta gct cat ttg cca
Leu Asp Ala Ser Gln Gln Ile Arg Leu Glu Ala Glu Glu Glu Lys Leu Ala His Leu Pro 2221 /     741                        2251 /     751
ctc gct aaa aca gta tcc gta gaa gag ctt ctg caa tac gtg gag ctt caa gat cct gtt
Leu Ala Lys Thr Val Ser Val Glu Glu Leu Leu Gln Tyr Val Glu Leu Gln Asp Pro Val 2281 /     761                        2311 /     771
acg cgc acg cag ctt cgc gca atg gct gct aaa acg gtc tgc ccg ccg cat aaa gta gag
Thr Arg Thr Gln Leu Arg Ala Met Ala Ala Lys Thr Val Cys Pro Pro His Lys Val Glu 2341 /     781                        2371 /     791
ctt gaa gcc ttg ctt gaa aag caa gcc tac aaa gaa caa gtg ctg gca aaa cgt tta aca
Leu Glu Ala Leu Leu Glu Lys Gln Ala Tyr Lys Glu Gln Val Leu Ala Lys Arg Leu Thr 2401 /     801                        2431 /     811
atg ctt gaa ctg ctt gaa aaa tac ccg gcg tgt gaa atg aaa ttc agc gaa ttt atc gcc
Met Leu Glu Leu Leu Glu Lys Tyr Pro Ala Cys Glu Met Lys Phe Ser Glu Phe Ile Ala 2461 /     821                        2491 /     831
ctt ctg cca agc ata cgc ccg cgc tat tac tcg att tct tca tca cct cgt gtc gat gaa
Leu Leu Pro Ser Ile Arg Pro Arg Tyr Tyr Ser Ile Ser Ser Ser Pro Arg Val Asp Glu 2521 /     841                        2551 /     851
aaa caa gca agc atc acg gtc acc gtt gtc tca gga gaa gcg tgg agc gga tat gga gaa
Lys Gln Ala Ser Ile Thr Val Ser Val Val Ser Gly Glu Ala Trp Ser Gly Tyr Gly Glu 2581 /     861                        2611 /     871
tat aaa gga att gcg tcg aac tat ctt gcc gag ctg caa gaa gga gat acg att acg tgc
Tyr Lys Gly Ile Ala Ser Asn Tyr Leu Ala Glu Leu Gln Glu Gly Asp Thr Ile Thr Cys 2641 /     881                        2671 /     891
ttt att tcc aca ccg cag tca gaa ttt acg ctg cca aaa gac cct gaa acg ccg ctt atc
Phe Ile Ser Thr Pro Gln Ser Glu Phe Thr Leu Pro Lys Asp Pro Glu Thr Pro Leu Ile 2701 /     901                        2731 /     911
atg gtc gga ccg gga aca ggc gtc gcg ccg ttt aga ggc ttt gtg cag gcg cgc aaa cag
Met Val Gly Pro Gly Thr Gly Val Ala Pro Phe Arg Gly Phe Val Gln Ala Arg Lys Gln 2761 /     921                        2791 /     931
cta aaa gaa caa gga cag tca ctt gga gaa gca cat tta tac ttc ggc tgc cgt tca cct
Leu Lys Glu Gln Gly Gln Ser Leu Gly Glu Ala His Leu Tyr Phe Gly Cys Arg Ser Pro 2821 /     941                        2851 /     951
cat gaa gac tat ctg tat caa gaa gag ctt gaa aac gcc caa agc gaa ggc atc att acg
His Glu Asp Tyr Leu Tyr Gln Glu Glu Leu Glu Asn Ala Gln Ser Glu Gly Ile Ile Thr 2881 /     961                        2911 /     971
ctt cat acc gct ttt tct cgc atg cca aat cag ccg aaa aca tac gtt cag cac gta atg
Leu His Thr Ala Phe Ser Arg Met Pro Asn Gln Pro Lys Thr Tyr Val Gln His Val Met 2941 /     981                        2971 /     991
gaa caa gac ggc aag aaa ttg att gaa ctt ctt gat caa gga gcg cac ttc tat att tgc
Glu Gln Asp Gly Lys Lys Leu Ile Glu Leu Leu Asp Gln Gly Ala His Phe Tyr Ile Cys 3001 /    1001                        3031 /    1011
gga gac gga agc caa atg gca cct gcc gtt gaa gca acg ctt atg aaa agc tat gct gac
Gly Asp Gly Ser Gln Met Ala Pro Ala Val Glu Ala Thr Leu Met Lys Ser Tyr Ala Asp
```

TABLE 8-continued

P450<sub>BM-3</sub> sequence

| 3061 / 1021 | | | | | | | 3091 / 1031 | | | | | | | | |
|---|---|---|---|---|---|---|---|---|---|---|---|---|---|---|---|
| gtt | cac | caa | gtg | agt | gaa | gca | gac | gct | cgc | tta | tgg | ctg | cag | cag | cta | gaa | gaa | aaa | ggc |
| Val | His | Gln | Val | Ser | Glu | Ala | Asp | Ala | Arg | Leu | Trp | Leu | Gln | Gln | Leu | Glu | Glu | Lys | Gly |

| 3121 / 1041 | | | | | | | | |
|---|---|---|---|---|---|---|---|---|
| cga | tac | gca | aaa | gac | gtg | tgg | gct | ggg | taa |
| Arg | Tyr | Ala | Lys | Asp | Val | Trp | Ala | Gly | OCH |

The invention claimed is:

1. A process for oxidizing a substrate wherein said substrate is a limonene or pinene or a cyclic sesquiterpene, wherein said limonene, pinene or cyclic sesquiterpene is optionally substituted by an alkyl of 1 to 6 carbons or an alkenyl of 1 to 6 carbons, and wherein the process comprises: oxidizing said substrate with a mutant haem-containing P450 enzyme, wherein said mutant enzyme is a mutant of a P450$_{BM-3}$ comprising the amino acid sequence of SEQ ID NO:24 and said mutant enzyme only has mutations at one or more of the following amino acid positions: 42, 51, 181, 263, 264 and 354 and wherein said mutant enzyme has a higher oxidation activity towards the substrate which is being oxidized than the enzyme having the sequence SEQ ID NO:24, and wherein at least one of said mutations is a substitution of an amino acid by another amino acid.

2. The process according to claim 1 in which the enzyme is one in which amino acid 51 of $P450_{BM-3}$ has been changed to another amino acid.

3. The process according to claim 1 in which the $P450_{BM-3}$ mutant comprises the mutation Y51F.

4. The process according to claim 1 in which the substrate is selected from the group consisting of limonene, pinene, and substituted derivatives thereof.

5. The process according to claim 1 in which the substrate is a cyclic sesquiterpene, or a substituted derivative thereof.

6. The process according to claim 5 in which the substrate is selected from the group consisting of aromadendrene, carophyllene, longifolene, valencene, isobazzanene, silphinene, ishwarane, isopatchchoul-3-ene, isosesquicarene, and substituted derivatives thereof.

* * * * *

SEQUENCE LISTING

<160> NUMBER OF SEQ ID NOS: 24

<210> SEQ ID NO 1
<211> LENGTH: 1242
<212> TYPE: DNA
<213> ORGANISM: Pseudomonas putida
<220> FEATURE:
<221> NAME/KEY: misc_feature
<222> LOCATION: (1)..(1242)
<223> OTHER INFORMATION: Coding Sequence

<400> SEQUENCE: 1

```
acgactgaaa ccatacaaag caacgccaat cttgcccctc tgccacccca tgtgccagag      60
cacctggtat tcgacttcga catgtacaat ccgtcgaatc tgtctgccgg cgtgcaggag     120
gcctgggcag ttctgcaaga atcaaacgta ccggatctgg tgtggactcg ctgcaacggc     180
ggacactgga tcgccactcg cggccaactg atccgtgagg cctatgaaga ttaccgccac     240
ttttccagcg agtgcccgtt catccctcgt gaagccggcg aagcctacga cttcattccc     300
acctcgatgg atccgcccga gcagcgccag tttcgtgcgc tggccaacca agtggttggc     360
atgccggtgg tggataagct ggagaaccgg atccaggagc tggcctgctc gctgatcgag     420
agcctgcgcc cgcaaggaca gtgcaacttc accgaggact acgccgaacc cttcccgata     480
cgcatcttca tgctgctcgc aggtctaccg gaagaagata tcccgcactt gaaataccta     540
acggatcaga tgacccgtcc ggatggcagc atgaccttcg cagaggccaa ggaggcgctc     600
tacgactatc tgataccgat catcgagcaa cgcaggcaga gccgggaac cgacgctatc     660 agcatcgttg ccaacggcca ggtcaatggg cgaccgatca ccagtgacga agccaagagg     720
atgtgtggcc tgttactggt cggcggcctg gatacggtgg tcaatttcct cagcttcagc     780
atggagttcc tggccaaaag cccggagcat cgccaggagc tgatcgagcg tcccgagcgt     840
attccagccg cttgcgagga actactccgg cgcttctcgc tggttgccga tggccgcatc     900
ctcacctccg attacgagtt tcatggcgtg caactgaaga aggtgaccca gatcctgcta     960
ccgcagatgc tgtctggcct ggatgagcgc gaaaacgcct gcccgatgca cgtcgacttc    1020
agtcgccaaa aggtttcaca caccacccttt ggccacggca gccatctgtg ccttggccag    1080
cacctggccc gccgggaaat catcgtcacc tcaaggaat ggctgaccag gattcctgac    1140
ttctccattg ccccgggtgc ccagattcag cacaagagcg gcatcgtcag cggcgtgcag    1200
gcactccctc tggtctggga tccggcgact accaaagcgg ta                        1242
```

<210> SEQ ID NO 2
<211> LENGTH: 3150
<212> TYPE: DNA
<213> ORGANISM: Bacillus megaterium
<220> FEATURE:

<221> NAME/KEY: misc_feature
<222> LOCATION: (1)..(3150)
<223> OTHER INFORMATION: Coding Sequence

<400> SEQUENCE: 2

| | | | | | |
|---|---|---|---|---|---|
| atgacaatta | aagaaatgcc | tcagccaaaa | acgtttggag | agcttaaaaa | tttaccgtta | 60 |
| ttaaacacag | ataaaccggt | tcaagctttg | atgaaaattg | cggatgaatt | aggagaaatc | 120 |
| tttaaattcg | aggcgcctgg | tcgtgtaacg | cgctacttat | caagtcagcg | tctaattaaa | 180 |
| gaagcatgcg | atgaatcacg | ctttgataaa | aacttaagtc | aagcgcttaa | atttgtacgt | 240 |
| gattttgcag | gagacgggtt | atttacaagc | tggacgcatg | aaaaaaattg | gaaaaaagcg | 300 |
| cataatatct | tacttccaag | cttcagtcag | caggcaatga | aaggctatca | tgcgatgatg | 360 |
| gtcgatatcg | ccgtgcagct | tgttcaaaag | tgggagcgtc | taaatgcaga | tgagcatatt | 420 |
| gaagtaccgg | aagacatgac | acgtttaacg | cttgatacaa | ttggtctttg | cggctttaac | 480 |
| tatcgcttta | acagctttta | ccgagatcag | cctcatccat | ttattacaag | tatggtccgt | 540 |
| gcactggatg | aagcaatgaa | caagctgcag | cgagcaaatc | cagacgaccc | agcttatgat | 600 |
| gaaaacaagc | gccagtttca | agaagatatc | aaggtgatga | cgacctagt | agataaaatt | 660 |
| attgcagatc | gcaaagcaag | cggtgaacaa | agcgatgatt | tattaacgca | tatgctaaac | 720 |
| ggaaaagatc | cagaaacggg | tgagccgctt | gatgacgaga | cattcgcta | tcaaattatt | 780 |
| acattcttaa | ttgcgggaca | cgaaacaaca | agtggtcttt | tatcatttgc | gctgtatttc | 840 |
| ttagtgaaaa | atccacatgt | attacaaaaa | gcagcagaag | aagcagcacg | agttctagta | 900 |
| gatcctgctc | caagctacaa | acaagtcaaa | cagcttaaat | atgtcggcat | ggtcttaaac | 960 |
| gaagcgctgc | gcttatggcc | aactgctcct | gcgttttccc | tatatgcaaa | agaagatacg | 1020 |
| gtgcttggag | gagaatatcc | tttagaaaaa | ggcgacgaac | taatggttct | gattcctcag | 1080 |
| cttcaccgtg | ataaaacaat | ttggggagac | gatgtggaag | agttccgtcc | agagcgtttt | 1140 |
| gaaaatccaa | gtgcgattcc | gcagcatgcg | tttaaaccgt | ttggaacgg | tcagcgtgcg | 1200 |
| tgtatcggtc | agcagttcgc | tcttcatgaa | gcaacgctgg | tacttggtat | gatgctaaaa | 1260 |
| cactttgact | ttgaagatca | tacaaactac | gagctggata | ttaaagaaac | tttaacgtta | 1320 |
| aaacctgaag | ctttgtggt | aaaagcaaaa | tcgaaaaaaa | ttccgcttgg | cggtattcct | 1380 |
| tcacctagca | ctgaacagtc | tgccaaaaaa | gcacgcaaaa | aggcagaaaa | cgctcataat | 1440 |
| acgccgctgc | ttgtgctata | cggttcaaat | atgggaacag | ctgaaggaac | ggcgcgtgat | 1500 |
| ttagcagata | ttgcaatgag | caaaggattt | gcaccgcagg | tcgcaacgct | tgattcacac | 1560 |
| gccggaaatc | ttccgcgcga | aggagctgta | ttaattgtaa | cggcgtctta | taacggtcat | 1620 |
| ccgcctgata | acgcaaagca | atttgtcgac | tggttagacc | aagcgtctgc | tgatgaagta | 1680 |
| aaaggcgttc | gctactccgt | atttggatgc | ggcgataaaa | actgggctac | tacgtatcaa | 1740 |
| aaagtgcctg | cttttatcga | tgaaacgctt | gccgctaaag | gggcagaaaa | catcgctgac | 1800 |
| cgcggtgaag | cagatgcaag | cgacgacttt | gaaggcacat | atgaagaatg | gcgtgaacat | 1860 |
| atgtggagtg | acgtagcagc | ctactttaac | ctcgacattg | aaaacagtga | agataataaa | 1920 |
| tctactcttt | cacttcaatt | tgtcgacagc | gccgcggata | tgccgcttgc | gaaaatgcac | 1980 |
| ggtgcgtttt | caacgaacgt | cgtagcaagc | aagaacttc | aacagccagg | cagtgcacga | 2040 |
| agcacgcgac | atcttgaaat | tgaacttcca | aaagaagctt | cttatcaaga | aggagatcat | 2100 |
| ttaggtgtta | ttcctcgcaa | ctatgaagga | atagtaaacc | gtgtaacagc | aaggttcggc | 2160 |
| ctagatgcat | cacagcaaat | ccgtctggaa | gcagaagaag | aaaaattagc | tcatttgcca | 2220 |

```
ctcgctaaaa cagtatccgt agaagagctt ctgcaatacg tggagcttca agatcctgtt    2280
acgcgcacgc agcttcgcgc aatggctgct aaaacggtct gcccgccgca taaagtagag    2340
cttgaagcct tgcttgaaaa gcaagcctac aaagaacaag tgctggcaaa acgtttaaca    2400
atgcttgaac tgcttgaaaa atacccggcg tgtgaaatga aattcagcga atttatcgcc    2460
cttctgccaa gcatacgccc gcgctattac tcgatttctt catcacctcg tgtcgatgaa    2520
aaacaagcaa gcatcacggt cagcgttgtc tcaggagaag cgtggagcgg atatggagaa    2580
tataaaggaa ttgcgtcgaa ctatcttgcc gagctgcaag aaggagatac gattacgtgc    2640
tttatttcca caccgcagtc agaatttacg ctgccaaaag accctgaaac gccgcttatc    2700
atggtcggac cgggaacagg cgtcgcgccg tttagaggct ttgtgcaggc gcgcaaacag    2760
ctaaaagaac aaggacagtc acttggagaa gcacatttat acttcggctg ccgttcacct    2820
catgaagact atctgtatca agaagagctt gaaaacgccc aaagcgaagg catcattacg    2880
cttcataccg cttttctcg catgccaaat cagccgaaaa catacgttca gcacgtaatg    2940
gaacaagacg gcaagaaatt gattgaactt cttgatcaag gagcgcactt ctatatttgc    3000
ggagacggaa gccaaatggc acctgccgtt gaagcaacgc ttatgaaaag ctatgctgac    3060
gttcaccaag tgagtgaagc agacgctcgc ttatggctgc agcagctaga agaaaaaggc    3120
cgatacgcaa aagacgtgtg ggctgggtaa                                     3150

<210> SEQ ID NO 3
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(7)
<223> OTHER INFORMATION: Linker

<400> SEQUENCE: 3

Thr Asp Gly Thr Ser Ser Thr
1               5

<210> SEQ ID NO 4
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(7)
<223> OTHER INFORMATION: Linker

<400> SEQUENCE: 4

Thr Asp Gly Ala Ser Ser Ser
1               5

<210> SEQ ID NO 5
<211> LENGTH: 17
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(17)
<223> OTHER INFORMATION: Linker
```

```
<400> SEQUENCE: 5

Thr Asp Gly Thr Arg Pro Gly Pro Gly Pro Gly Pro Ser Ser
1               5                   10                  15

Thr

<210> SEQ ID NO 6
<211> LENGTH: 21
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(21)
<223> OTHER INFORMATION: Linker

<400> SEQUENCE: 6

Thr Asp Gly Thr Arg Pro Gly Pro Gly Pro Gly Pro Gly Pro
1               5                   10                  15

Gly Pro Ser Ser Thr
            20

<210> SEQ ID NO 7
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(4)
<223> OTHER INFORMATION: Linker

<400> SEQUENCE: 7

Pro Leu Glu Leu
1

<210> SEQ ID NO 8
<211> LENGTH: 7
<212> TYPE: PRT
<213> ORGANISM: Artificial Sequence
<220> FEATURE:
<223> OTHER INFORMATION: Linker
<220> FEATURE:
<221> NAME/KEY: DOMAIN
<222> LOCATION: (1)..(7)
<223> OTHER INFORMATION: Linker

<400> SEQUENCE: 8

Thr Asp Gly Gly Ser Ser Ser
1               5

<210> SEQ ID NO 9
<211> LENGTH: 51
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(51)
<223> OTHER INFORMATION: Primer

<400> SEQUENCE: 9
gagattaaga attcataaac acatgggagt gcgtgccata tgaacgcaaa c        51

<210> SEQ ID NO 10
```

```
<211> LENGTH: 36
<212> TYPE: DNA
<213> ORGANISM: Artificial Sequence
<220> FEATURE:
<223> OTHER INFORMATION: Coding Sequence
<220> FEATURE:
<221> NAME/KEY: variation
<222> LOCATION: (1)..(36)
<223> OTHER INFORMATION: Desired coding sequence

<400> SEQUENCE: 10
gaactgagta gtgccactga cggaggatcc tcatcg                              36

<210> SEQ ID NO 11
<211> LENGTH: 36
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(36)
<223> OTHER INFORMATION: Primer

<400> SEQUENCE: 11
cgatgaggat cctccgtcag tggcactact cagttc                              36

<210> SEQ ID NO 12
<211> LENGTH: 36
<212> TYPE: DNA
<213> ORGANISM: ARTIFICIAL SEQUENCE
<220> FEATURE:
<223> OTHER INFORMATION: Primer
<220> FEATURE:
<221> NAME/KEY: misc_feature
<222> LOCATION: (1)..(36)
<223> OTHER INFORMATION: Primer

<400> SEQUENCE: 12
tcatcgggat cctcatcgat gtctaaagta gtgtat                              36

<210> SEQ ID NO 13
<211> LENGTH: 52
<212> TYPE: DNA
<213> ORGANISM: Artificial Sequence
<220> FEATURE:
<223> OTHER INFORMATION: Desired Coding Sequence
<220> FEATURE:
<221> NAME/KEY: misc_feature
<222> LOCATION: (1)..(52)
<223> OTHER INFORMATION: Desired Coding Sequence

<400> SEQUENCE: 13
cccgataggc aatggtaatc atcgggagtc tagagcatcg aagctttcat cg            52

<210> SEQ ID NO 14
<211> LENGTH: 52
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(52)
<223> OTHER INFORMATION: Primer

<400> SEQUENCE: 14
cgatgaaagc ttcgatgctc tagactcccg atgattacca ttgcctatcg gg            52
```

```
<210> SEQ ID NO 15
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: Primer

<400> SEQUENCE: 15
tcatcgacgc gtcgcgaact gctg                                          24

<210> SEQ ID NO 16
<211> LENGTH: 69
<212> TYPE: DNA
<213> ORGANISM: Artificial Sequence
<220> FEATURE:
<223> OTHER INFORMATION: Desired Coding Sequence
<220> FEATURE:
<221> NAME/KEY: misc_feature
<222> LOCATION: (1)..(69)
<223> OTHER INFORMATION: Desired Coding Sequence

<400> SEQUENCE: 16
cccgataggc aatggtaagt aggtgaatat ctaatcccca tctatgcgcg agtggagtct    60
agagttcga                                                           69

<210> SEQ ID NO 17
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: Primer

<400> SEQUENCE: 17
tcatcgaagc ttggctgttt t                                             21

<210> SEQ ID NO 18
<211> LENGTH: 47
<212> TYPE: DNA
<213> ORGANISM: Artificial Sequence
<220> FEATURE:
<223> OTHER INFORMATION: Desired Coding Sequence
<220> FEATURE:
<221> NAME/KEY: misc_feature
<222> LOCATION: (1)..(47)
<223> OTHER INFORMATION: Desired Coding Sequence

<400> SEQUENCE: 18
acaatttcac acaggatcta gaccatatgt catcgaagct ttcatcg                 47

<210> SEQ ID NO 19
<211> LENGTH: 47
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(47)
<223> OTHER INFORMATION: Primer

<400> SEQUENCE: 19
```
cgatgaaagc ttcgatgaca tatggtctag atcctgtgtg aaattgt    47

<210> SEQ ID NO 20
<211> LENGTH: 414
<212> TYPE: PRT
<213> ORGANISM: Pseudomonas putida
<220> FEATURE:
<221> NAME/KEY: MUTAGEN
<222> LOCATION: (1)..(414)
<223> OTHER INFORMATION: Coding sequence

<400> SEQUENCE: 20

```
Thr Thr Glu Thr Ile Gln Ser Asn Ala Asn Leu Ala Pro Leu Pro Pro
1               5                   10                  15

His Val Pro Glu His Leu Val Phe Asp Phe Asp Met Tyr Asn Pro Ser
            20                  25                  30

Asn Leu Ser Ala Gly Val Gln Glu Ala Trp Ala Val Leu Gln Glu Ser
        35                  40                  45

Asn Val Pro Asp Leu Val Trp Thr Arg Cys Asn Gly Gly His Trp Ile
    50                  55                  60

Ala Thr Arg Gly Gln Leu Ile Arg Glu Ala Tyr Glu Asp Tyr Arg His
65                  70                  75                  80

Phe Ser Ser Glu Cys Pro Phe Ile Pro Arg Glu Ala Gly Glu Ala Tyr
                85                  90                  95

Asp Phe Ile Pro Thr Ser Met Asp Pro Pro Glu Gln Arg Gln Phe Arg
            100                 105                 110

Ala Leu Ala Asn Gln Val Val Gly Met Pro Val Val Asp Lys Leu Glu
        115                 120                 125

Asn Arg Ile Gln Glu Leu Ala Cys Ser Leu Ile Glu Ser Leu Arg Pro
    130                 135                 140

Gln Gly Gln Cys Asn Phe Thr Glu Asp Tyr Ala Glu Pro Phe Pro Ile
145                 150                 155                 160

Arg Ile Phe Met Leu Leu Ala Gly Leu Pro Glu Glu Asp Ile Pro His
                165                 170                 175

Leu Lys Tyr Leu Thr Asp Gln Met Thr Arg Pro Asp Gly Ser Met Thr
            180                 185                 190

Phe Ala Glu Ala Lys Glu Ala Leu Tyr Asp Tyr Leu Ile Pro Ile Ile
        195                 200                 205

Glu Gln Arg Arg Gln Lys Pro Gly Thr Asp Ala Ile Ser Ile Val Ala
    210                 215                 220

Asn Gly Gln Val Asn Gly Arg Pro Ile Thr Ser Asp Glu Ala Lys Arg
225                 230                 235                 240

Met Cys Gly Leu Leu Leu Val Gly Gly Leu Asp Thr Val Val Asn Phe
                245                 250                 255

Leu Ser Phe Ser Met Glu Phe Leu Ala Lys Ser Pro Glu His Arg Gln
            260                 265                 270

Glu Leu Ile Glu Arg Pro Glu Arg Ile Pro Ala Ala Cys Glu Glu Leu
        275                 280                 285

Leu Arg Arg Phe Ser Leu Val Ala Asp Gly Arg Ile Leu Thr Ser Asp
    290                 295                 300

Tyr Glu Phe His Gly Val Gln Leu Lys Lys Gly Asp Gln Ile Leu Leu
305                 310                 315                 320

Pro Gln Met Leu Ser Gly Leu Asp Glu Arg Glu Asn Ala Cys Pro Met
                325                 330                 335

His Val Asp Phe Ser Arg Gln Lys Val Ser His Thr Thr Phe Gly His
            340                 345                 350
```

-continued

Gly Ser His Leu Cys Leu Gly Gln His Leu Ala Arg Arg Glu Ile Ile
        355                 360                 365

Val Thr Leu Lys Glu Trp Leu Thr Arg Ile Pro Asp Phe Ser Ile Ala
    370                 375                 380

Pro Gly Ala Gln Ile Gln His Lys Ser Gly Ile Val Ser Gly Val Gln
385                 390                 395                 400

Ala Leu Pro Leu Val Trp Asp Pro Ala Thr Thr Lys Ala Val
                405                 410

<210> SEQ ID NO 21
<211> LENGTH: 1049
<212> TYPE: PRT
<213> ORGANISM: bacillus megaterium
<220> FEATURE:
<221> NAME/KEY: MUTAGEN
<222> LOCATION: (1)..(1049)
<223> OTHER INFORMATION: Coding Sequence

<400> SEQUENCE: 21

Met Thr Ile Lys Glu Met Pro Gln Pro Lys Thr Phe Gly Glu Leu Lys
1               5                   10                  15

Asn Leu Pro Leu Leu Asn Thr Asp Lys Pro Val Gln Ala Leu Met Lys
            20                  25                  30

Ile Ala Asp Glu Leu Gly Glu Ile Phe Lys Phe Glu Ala Pro Gly Arg
        35                  40                  45

Val Thr Arg Tyr Leu Ser Ser Gln Arg Leu Ile Lys Glu Ala Cys Asp
    50                  55                  60

Glu Ser Arg Phe Asp Lys Asn Leu Ser Gln Ala Leu Lys Phe Val Arg
65                  70                  75                  80

Asp Phe Ala Gly Asp Gly Leu Phe Thr Ser Trp Thr His Glu Lys Asn
                85                  90                  95

Trp Lys Lys Ala His Asn Ile Leu Leu Pro Ser Phe Ser Gln Gln Ala
            100                 105                 110

Met Lys Gly Tyr His Ala Met Met Val Asp Ile Ala Val Gln Leu Val
        115                 120                 125

Gln Lys Trp Glu Arg Leu Asn Ala Asp Glu His Ile Glu Val Pro Glu
    130                 135                 140

Asp Met Thr Arg Leu Thr Leu Asp Thr Ile Gly Leu Cys Gly Phe Asn
145                 150                 155                 160

Tyr Arg Phe Asn Ser Phe Tyr Arg Asp Gln Pro His Pro Phe Ile Thr
                165                 170                 175

Ser Met Val Arg Ala Leu Asp Glu Ala Met Asn Lys Leu Gln Arg Ala
        180                 185                 190

Asn Pro Asp Asp Pro Ala Tyr Asp Glu Asn Lys Arg Gln Phe Gln Glu
    195                 200                 205

Asp Ile Lys Val Met Asn Asp Leu Val Asp Lys Ile Ile Ala Asp Arg
210                 215                 220

Lys Ala Ser Gly Glu Gln Ser Asp Asp Leu Leu Thr His Met Leu Asn
225                 230                 235                 240

Gly Lys Asp Pro Glu Thr Gly Glu Pro Leu Asp Asp Glu Asn Ile Arg
                245                 250                 255

Tyr Gln Ile Ile Thr Phe Leu Ile Ala Gly His Glu Thr Thr Ser Gly
        260                 265                 270

Leu Leu Ser Phe Ala Leu Tyr Phe Leu Val Lys Asn Pro His Val Leu
    275                 280                 285

```
Gln Lys Ala Ala Glu Ala Ala Arg Val Leu Val Asp Pro Ala Pro
    290                 295                 300

Ser Tyr Lys Gln Val Lys Gln Leu Lys Tyr Val Gly Met Val Leu Asn
305                 310                 315                 320

Glu Ala Leu Arg Leu Trp Pro Thr Ala Pro Ala Phe Ser Leu Tyr Ala
                325                 330                 335

Lys Glu Asp Thr Val Leu Gly Gly Tyr Pro Leu Glu Lys Gly Asp
            340                 345                 350

Glu Leu Met Val Leu Ile Pro Gln Leu His Arg Asp Lys Thr Ile Trp
        355                 360                 365

Gly Asp Val Glu Glu Phe Arg Pro Glu Arg Phe Glu Asn Pro Ser
    370                 375                 380

Ala Ile Pro Gln His Ala Phe Lys Pro Phe Gly Asn Gly Gln Arg Ala
385                 390                 395                 400

Cys Ile Gly Gln Gln Phe Ala Leu His Glu Ala Thr Leu Val Leu Gly
                405                 410                 415

Met Met Leu Lys His Phe Asp Phe Glu Asp His Thr Asn Tyr Glu Leu
            420                 425                 430

Asp Ile Lys Glu Thr Leu Thr Leu Lys Pro Glu Gly Phe Val Val Lys
        435                 440                 445

Ala Lys Ser Lys Lys Ile Pro Leu Gly Gly Ile Pro Ser Pro Ser Thr
    450                 455                 460

Glu Gln Ser Ala Lys Lys Ala Arg Lys Lys Ala Glu Asn Ala His Asn
465                 470                 475                 480

Thr Pro Leu Leu Val Leu Tyr Gly Ser Asn Met Gly Thr Ala Glu Gly
                485                 490                 495

Thr Ala Arg Asp Leu Ala Asp Ile Ala Met Ser Lys Gly Phe Ala Pro
            500                 505                 510

Gln Val Ala Thr Leu Asp Ser His Ala Gly Asn Leu Pro Arg Glu Gly
        515                 520                 525

Ala Val Leu Ile Val Thr Ala Ser Tyr Asn Gly His Pro Pro Asp Asn
    530                 535                 540

Ala Lys Gln Phe Val Asp Trp Leu Asp Gln Ala Ser Ala Asp Glu Val
545                 550                 555                 560

Lys Gly Val Arg Tyr Ser Val Phe Gly Cys Gly Asp Lys Asn Trp Ala
                565                 570                 575

Thr Thr Tyr Gln Lys Val Pro Ala Phe Ile Asp Glu Thr Leu Ala Ala
            580                 585                 590

Lys Gly Ala Glu Asn Ile Ala Asp Arg Gly Glu Ala Asp Ala Ser Asp
        595                 600                 605

Asp Phe Glu Gly Thr Tyr Glu Glu Trp Arg Glu His Met Trp Ser Asp
    610                 615                 620

Val Ala Ala Tyr Phe Asn Leu Asp Ile Glu Asn Ser Glu Asp Asn Lys
625                 630                 635                 640

Ser Thr Leu Ser Leu Gln Phe Val Asp Ser Ala Ala Asp Met Pro Leu
                645                 650                 655

Ala Lys Met His Gly Ala Phe Ser Thr Asn Val Val Ala Ser Lys Glu
            660                 665                 670

Leu Gln Gln Pro Gly Ser Ala Arg Ser Thr Arg His Leu Glu Ile Glu
        675                 680                 685

Leu Pro Lys Glu Ala Ser Tyr Gln Glu Gly Asp His Leu Gly Val Ile
    690                 695                 700

Pro Arg Asn Tyr Glu Gly Ile Val Asn Arg Val Thr Ala Arg Phe Gly
```

-continued

```
            705                 710                 715                 720
    Leu Asp Ala Ser Gln Gln Ile Arg Leu Glu Ala Glu Glu Lys Leu
                    725                 730                 735
    Ala His Leu Pro Leu Ala Lys Thr Val Ser Val Glu Glu Leu Leu Gln
                    740                 745                 750
    Tyr Val Glu Leu Gln Asp Pro Val Thr Arg Thr Gln Leu Arg Ala Met
                    755                 760                 765
    Ala Ala Lys Thr Val Cys Pro Pro His Lys Val Glu Leu Glu Ala Leu
                    770                 775                 780
    Leu Glu Lys Gln Ala Tyr Lys Glu Gln Val Leu Ala Lys Arg Leu Thr
    785                 790                 795                 800
    Met Leu Glu Leu Leu Glu Lys Tyr Pro Ala Cys Glu Met Lys Phe Ser
                    805                 810                 815
    Glu Phe Ile Ala Leu Leu Pro Ser Ile Arg Pro Arg Tyr Tyr Ser Ile
                    820                 825                 830
    Ser Ser Ser Pro Arg Val Asp Glu Lys Gln Ala Ser Ile Thr Val Ser
                    835                 840                 845
    Val Val Ser Gly Glu Ala Trp Ser Gly Tyr Gly Glu Tyr Lys Gly Ile
                    850                 855                 860
    Ala Ser Asn Tyr Leu Ala Glu Leu Gln Glu Gly Asp Thr Ile Thr Cys
    865                 870                 875                 880
    Phe Ile Ser Thr Pro Gln Ser Glu Phe Thr Leu Pro Lys Asp Pro Glu
                    885                 890                 895
    Thr Pro Leu Ile Met Val Gly Pro Gly Thr Gly Val Ala Pro Phe Arg
                    900                 905                 910
    Gly Phe Val Gln Ala Arg Lys Gln Leu Lys Glu Gln Gly Gln Ser Leu
                    915                 920                 925
    Gly Glu Ala His Leu Tyr Phe Gly Cys Arg Ser Pro His Glu Asp Tyr
                    930                 935                 940
    Leu Tyr Gln Glu Glu Leu Glu Asn Ala Gln Ser Glu Gly Ile Ile Thr
    945                 950                 955                 960
    Leu His Thr Ala Phe Ser Arg Met Pro Asn Gln Pro Lys Thr Tyr Val
                    965                 970                 975
    Gln His Val Met Glu Gln Asp Gly Lys Lys Leu Ile Glu Leu Leu Asp
                    980                 985                 990
    Gln Gly Ala His Phe Tyr Ile Cys Gly Asp Gly Ser Gln Met Ala Pro
                    995                 1000                1005
    Ala Val Glu Ala Thr Leu Met Lys Ser Tyr Ala Asp Val His Gln
            1010                1015                1020
    Val Ser Glu Ala Asp Ala Arg Leu Trp Leu Gln Gln Leu Glu Glu
            1025                1030                1035
    Lys Gly Arg Tyr Ala Lys Asp Val Trp Ala Gly
            1040                1045

<210> SEQ ID NO 22
<211> LENGTH: 5
<212> TYPE: PRT
<213> ORGANISM: Artificial sequence
<220> FEATURE:
<223> OTHER INFORMATION: Coding Sequence
<220> FEATURE:
<221> NAME/KEY: MUTAGEN
<222> LOCATION: (1)..(5)
<223> OTHER INFORMATION: Coding Sequence

<400> SEQUENCE: 22
```

-continued

```
Thr Asp Gly Gly Ser
1               5

<210> SEQ ID NO 23
<211> LENGTH: 2
<212> TYPE: PRT
<213> ORGANISM: Artificial Sequence
<220> FEATURE:
<223> OTHER INFORMATION: Primer
<220> FEATURE:
<221> NAME/KEY: MUTAGEN
<222> LOCATION: (1)..(2)
<223> OTHER INFORMATION: Primer

<400> SEQUENCE: 23

Gly Ser
1

<210> SEQ ID NO 24
<211> LENGTH: 1048
<212> TYPE: PRT
<213> ORGANISM: Bacillus megaterium
<220> FEATURE:
<221> NAME/KEY: MUTAGEN
<222> LOCATION: (1)..(1048)
<223> OTHER INFORMATION: Coding Sequence

<400> SEQUENCE: 24

Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255
```

```
Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Ala Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Ala Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670
```

```
Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
        690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
        740                 745                 750

Val Glu Leu Gln Asp Pro Val Thr Arg Thr Gln Leu Arg Ala Met Ala
        755                 760                 765

Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
            805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
        835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
            885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
        915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
            965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
        995                1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045
```